(12) United States Patent
Fontanier et al.

(10) Patent No.: US 11,492,355 B2
(45) Date of Patent: Nov. 8, 2022

(54) CROSSLINKING COMPOUND, METHOD FOR SYNTHESIZING SAME, LIQUID COMPOSITION COMPRISING SAID CROSSLINKING COMPOUND, PROCESS FOR POLYMERIZING SAME, AND MATERIAL OBTAINED AFTER POLYMERIZATION

(71) Applicant: Arkema France, Colombes (FR)

(72) Inventors: Jean-Charles Fontanier, Albi (FR); Jean-Francois Gerard, Bron (FR); Pierre Gerard, Denguin (FR); Frederic Lortie, Villeurbanne (FR); Jean-Pierre Pascault, Villeurbanne (FR)

(73) Assignee: ARKEMA FRANCE, Colombes (FR)

( * ) Notice: Subject to any disclaimer, the term of this patent is extended or adjusted under 35 U.S.C. 154(b) by 100 days.

(21) Appl. No.: 16/492,998

(22) PCT Filed: Mar. 27, 2018

(86) PCT No.: PCT/FR2018/050736
§ 371 (c)(1),
(2) Date: Sep. 11, 2019

(87) PCT Pub. No.: WO2018/178556
PCT Pub. Date: Oct. 4, 2018

(65) Prior Publication Data
US 2020/0115385 A1  Apr. 16, 2020

(30) Foreign Application Priority Data
Mar. 27, 2017 (FR) ...................................... 17 52544

(51) Int. Cl.
*C07D 491/18* (2006.01)
*C08F 20/06* (2006.01)
*C08K 5/3415* (2006.01)
*C08L 33/10* (2006.01)

(52) U.S. Cl.
CPC ............ *C07D 491/18* (2013.01); *C08F 20/06* (2013.01); *C08K 5/3415* (2013.01); *C08L 33/10* (2013.01)

(58) Field of Classification Search
CPC ..... C07D 491/18; C08F 20/06; C08K 5/3415; C08L 33/10
USPC ....................................................... 548/435
See application file for complete search history.

(56) References Cited

U.S. PATENT DOCUMENTS

| | | |
|---|---|---|
| 9,777,140 B2 | 10/2017 | Gerard et al. |
| 10,040,889 B2 | 8/2018 | Gerard et al. |
| 10,294,358 B2 | 5/2019 | Gerard et al. |
| 2011/0190458 A1 | 8/2011 | Broekhuis et al. |
| 2014/0256850 A1 | 9/2014 | Gerard et al. |
| 2018/0009968 A1 | 1/2018 | Gerard et al. |
| 2018/0371209 A1 | 12/2018 | Gerard et al. |

FOREIGN PATENT DOCUMENTS

| | | | | |
|---|---|---|---|---|
| CN | 105294936 A | | 2/2016 | |
| GB | 2453112 A | * | 4/2009 | ............ C08F 220/58 |
| JP | 2005 232412 A | | 9/2005 | |

(Continued)

OTHER PUBLICATIONS

English translation of Japanese Patent Publication JP-4397249-B2 (Year: 2021).*

*Primary Examiner* — Joseph R Kosack
*Assistant Examiner* — Sagar Patel
(74) *Attorney, Agent, or Firm* — Buchanan Ingersoll & Rooney P.C.

(57) ABSTRACT

The invention relates to a crosslinking compound of formula (I)

Figure 1:
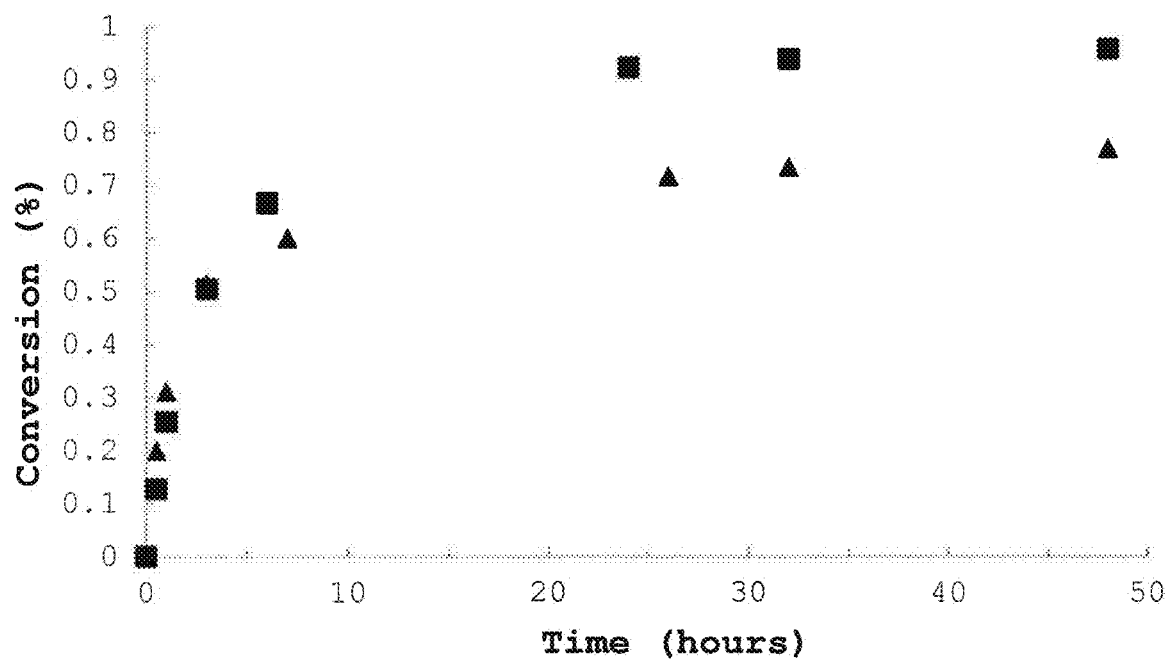

In particular, the present invention relates to a liquid composition comprising a monomer, a (meth)acrylic polymer and at least one crosslinking compound of formula (I). This liquid composition may be used in the form of a syrup and in particular in the form of a syrup for impregnating fibers or fibrous material. The invention also relates to a pseudo-thermoplastic material obtained after polymerization of the liquid composition being at least partially crosslinked. The invention also relates to a process for manufacturing such a liquid composition. The invention also relates to a process for impregnating a long-fiber fibrous substrate with said liquid composition. The invention also relates to a fibrous substrate impregnated with said liquid composition which is useful for manufacturing composite parts. The present invention also relates to a process for manufacturing mechanical parts or structural elements made of composite material and to mechanical parts or structural elements made of composite material obtained via a process using such a liquid composition.

22 Claims, 2 Drawing Sheets

(56) References Cited

FOREIGN PATENT DOCUMENTS

| | | | |
|---|---|---|---|
| JP | 2005 232412 | A2 | 9/2005 |
| JP | 4397249 | B2 * | 1/2010 |
| JP | 2014 169384 | A | 9/2014 |
| JP | 2014 169384 | A2 | 9/2014 |
| WO | WO-2014174098 | A1 * | 10/2014 ............ C08F 265/06 |

* cited by examiner

CROSSLINKING COMPOUND, METHOD FOR SYNTHESIZING SAME, LIQUID COMPOSITION COMPRISING SAID CROSSLINKING COMPOUND, PROCESS FOR POLYMERIZING SAME, AND MATERIAL OBTAINED AFTER POLYMERIZATION

This application claims benefit, under U.S.C. § 119 or § 365 of PCT Application Number PCT/FR2018/050736, filed Mar. 27, 2018, and French Patent Applications Number FR 17.52544, filed Mar. 27, 2017, these documents being incorporated herein by reference.

The invention relates to the field of thermoplastic polymers and more particularly composite materials comprising thermoplastic polymers. The present invention relates to a crosslinking compound, to the process for synthesizing same and also to a liquid composition comprising a monomer, a (meth)acrylic polymer and said crosslinking compound. This liquid composition may be used in the form of a syrup in particular for impregnating fibers or fibrous material. The invention also relates to a thermoplastic material obtained after polymerization of the liquid composition. The invention also relates to a process for impregnating a long-fiber fibrous substrate with said liquid composition. The invention also relates to a fibrous substrate impregnated with said liquid composition which is useful for manufacturing composite parts. The present invention also relates to a process for manufacturing mechanical parts or structural elements made of composite material and mechanical parts obtained via a process using such a liquid composition.

PRIOR ART

Thermoplastic polymers are materials that are widely used nowadays in several fields such as the construction, aeronautical, motor vehicle or railway sectors, in which they form part of mechanical parts. These mechanical parts, which include thermoplastic polymers, may withstand high chemical or mechanical stresses during their use and are generally manufactured from composite materials. A composite material is a macroscopic combination of two or more than two immiscible materials. Composite material are generally constituted of at least one material which forms the matrix, i.e. a continuous phase that ensures the cohesion of the structure, and of a reinforcing material. The use of a composite material makes it possible to obtain performance qualities that are not available from each of its constituents when they are used separately. Consequently, and notably on account of their better mechanical performance qualities (higher tensile strength, higher tensile modulus, higher toughness) and their low mass per unit volume relative to homogeneous materials, composite materials are widely used in industrial sectors such as construction, motor vehicles, aerospace, transportation, leisure, electronics and sports.

In these sectors, the composite materials used are often based on thermosetting polymers since said polymers have advantageous mechanical properties and physicochemical characteristics, such as resistance to solvents, which are desirable in many fields of application.

Nevertheless, in order to allow thermoforming and recycling, it is preferable to use, in composite materials, thermoplastic polymers. Thermoplastic polymers are constituted of linear or branched polymers, which are usually not crosslinked. For example, a liquid composition or a syrup comprising a (meth)acrylic monomer and a (meth)acrylic polymer is described in WO 2013/056845, WO 2014/013028 and WO 2014/174098.

However, materials including thermoplastic polymers may have a certain sensitivity to solvents when compared with thermosetting materials. Thus, in recent years, numerous studies regarding the development of reversible networks have been conducted based notably on Diels-Alder (DA) and retro-Diels-Alder (rDA) reactions. Specifically, besides the wide field of possible applications, these "reversible" networks are very advantageous since they make it possible to go easily from a three-dimensional polymer to a linear polymer. This type of network is obtained, for example, by addition of a conjugated diene to a dienophile.

The proposed strategies generally consist in governing the formation of the network by DA reaction by reacting a dienophile with a conjugated diene incorporated in a polymer chain or else by reacting together a diene/dienophile multifunctional monomer pair so as to form the crosslinked polymer. Thus, as is detailed in WO 2010/033028, a copolymer bearing furan side functions, which, in the presence of a bisdienophile, at a suitable temperature, makes it possible by DA reaction to bridge two polymer chains together, thus leading to the production of a three-dimensional network. Next, when heated to a suitable temperature, the DA addition reaction becomes reversible and allows the initial products to be regained. In said document, the fastest crosslinking time was about 2 hours. Thus, this technique is not suited to industrial use. Specifically, the kinetics of this reaction are too slow and the degree of conversion is low.

In addition, this absence of complete conversion leads to the presence in the final polymer material of a portion of unreacted dienophile or conjugated diene compounds which may lead to uncontrolled subsequent reactivity.

Thus, there is a need for novel crosslinking compounds and liquid compositions for the formation of thermoplastic polymers that can satisfy the problems generated by the existing methods.

TECHNICAL PROBLEM

One object of the present invention is to provide a crosslinking compound that is capable of improving the mechanical and physicochemical properties of thermoplastic polymers. Another object of the present invention is to provide a liquid composition comprising a monomer, a (meth)acrylic polymer and a crosslinking compound to obtain a composition that can be used in industrial processes requiring short production cycles, for example less than five minutes.

An object of the present invention is also to provide a process for forming a thermoplastic polymer that is at least partially crosslinked with good conversion, i.e. which includes less than 5% of conjugated diene and dienophile functions, capable of undergoing a Diels-Aider addition reaction, which are free, i.e. which have not undergone a Diels-Alder addition reaction.

Another subject of the present invention is to propose a process that can be performed at low cost and which allows the industrial-scale manufacture of mechanical parts or structural elements constituted of at least partially crosslinked thermoplastic polymer or of at least partially crosslinked thermoplastic composite material. The manufacture of the composite parts should also be reproducible and fast, meaning short cycle times.

BRIEF DESCRIPTION OF THE INVENTION

To this end, the invention relates to a crosslinking compound of formula (I)

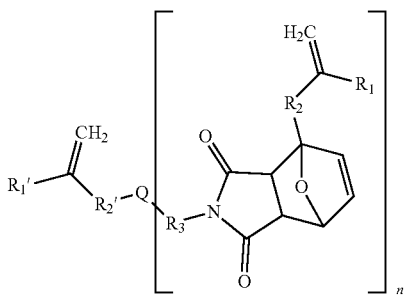

(I)

in which:
the group Q represents -Z-L- in which
the group Z represents a single bond or

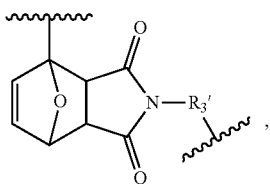

the group L represents a single bond or a group selected from: —(C$_1$-C$_6$)alkyl-, —(C$_2$-C$_6$)alkenyl-, —(C$_2$-C$_6$)alkynyl-, —(CONHR$_4$NHCOOR$_5$O)$_m$—, —(O—CO—NR$_6$)$_m$—, (OR$_4$CHOHR$_5$)$_m$—, —(CH$_2$CHOHCH$_2$OR$_4$O)$_m$—, —(OR$_4$)$_m$—, —((CHOR$_6$)CH$_2$O—R$_4$)$_m$—, —(R$_4$—COO—R$_5$)$_m$—, —NR$_6$—, —SO$_2$—, —SO$_2$NR$_6$—, —O—, —S—, —CONR$_6$—, -aryl-, -(aryl-R$_4$)$_m$-, -(heteroaryl-R$_4$)$_m$-, —((C$_3$-C$_8$)heterocyclyl-R$_4$)$_m$—, —((C$_3$-C$_{14}$)cycloalkyl-R$_4$)$_m$—, —(C$_1$-C$_6$)alkyl-R$_7$—(C$_1$-C$_6$)alkyl-, —(C$_2$-C$_6$)alkenyl-R$_7$—(C$_1$-C$_6$) alkyl-, —(C$_1$-C$_6$)alkyl-R$_7$—(C$_2$-C$_6$)alkenyl-, or —(C$_2$-C$_6$)alkenyl-R$_7$—(C$_2$-C$_6$)alkenyl-,
in which the groups R$_4$ and R$_5$ are identical or different and represent a group selected from: single bond, —(C$_1$-C$_6$)alkyl-, —(C$_2$-C$_6$)alkenyl-, —NR$_6$—, —SO$_2$—, —SO$_2$NR$_6$—, —O—, —S—, —CONR$_6$—, -aryl-, -(aryl-R$_6$)$_m$—, -(heteroaryl-R$_6$)$_m$—, —((C$_3$-C$_8$)heterocyclyl)-R$_6$)$_m$—, —((C$_3$-C$_{14}$)cycloalkyl-R$_6$)$_m$-aryl-, -heteroaryl-, —(C$_3$-C$_8$)heterocyclyl-, —(C$_3$-C$_{14}$)cycloalkyl-, —(C$_1$-C$_6$)alkyl-OCO—, or —CH$_2$—(CHOR$_3$)CH$_2$O—(C$_1$-C$_6$)alkyl-;
in which R$_6$ represents a group selected from: hydrogen atom, —(C$_1$-C$_6$)alkyl, —(C$_2$-C$_6$)alkenyl, —NH$_2$, —COOH, —SO$_2$H, —OH, —SH, -aryl, heteroaryl, —(C$_3$-C$_8$)heterocyclyl, or —(C$_3$-C$_{14}$) cycloalkyl;
in which R$_7$ represents a group selected from: single bond, —(CONHR$_4$NHCOOR$_5$O)$_m$—, —(O—CO—NR$_4$)$_m$—, —(COR$_4$)$_m$—, —(OR$_4$)$_m$—, —(CH$_2$CHOHCH$_2$OR$_4$O)$_m$—, —((CHOR$_4$)CH$_2$O—R$_5$)$_m$—, —(R$_4$—COO—R$_5$)$_m$—, —NR$_6$—, —SO$_2$—, —SO$_2$NR$_6$—, —O—, —S—, —CONR$_6$—, -aryl-, -(aryl-R$_4$)$_m$—, -(heteroaryl-R$_4$)$_m$—, —((C$_3$-C$_8$)heterocyclyl)-R$_4$)$_m$—, —((C$_3$-C$_{14}$)cycloalkyl-R$_4$)$_m$—, —(C$_1$-C$_6$)alkyl-OCO—, or —CH$_2$—(CHOR$_3$)CH$_2$O—(C$_1$-C$_6$)alkyl-;

the groups R$_1$ and R$_1$' are identical or different and represent a hydrogen atom or an alkyl group bearing a linear or branched chain containing up to 6 carbon atoms;
the groups R$_2$ and R$_2$' are identical or different and represent a single bond or a group selected from: —(C$_1$-C$_6$)alkyl-, —(C$_2$-C$_6$)alkenyl-, —COO—, or —(C$_1$-C$_6$)alkyl-COO—, preferably —COO— or —(C$_1$-C$_6$)alkyl-COO—;
the groups R$_3$ and R$_3$' are identical or different and represent a single bond or a group selected from: —(C$_1$-C$_6$)alkyl-, —(C$_2$-C$_6$)alkenyl-, —NHCOO—, preferably —NHCOO—;
with n representing the number of repeating units, between 1 and 10,
with m representing the number of repeating units, between 1 and 20, for example between 1 and 10.

This crosslinking compound includes two polymerizable vinyl functions and at least one Diels-Alder adduct corresponding to a group that is capable of undergoing a retro-Diets-Alder reaction.

The choice of the group "L" makes it possible to vary the properties of the crosslinking compound and more broadly of a pseudo-thermoplastic polymer which may be obtained from said compound. Specifically, the spacer "L" gives the final network different properties, Thus, a spacer "L" bearing a long carbon chain between its two maleimide functions allows the formation of a flexible and poorly heat-resistant network. Conversely, a short structure bearing one or more aromatic nuclei will be the source of a rigid and heat-resistant network.

As shall be presented in the continuation of the application, this crosslinking compound may include a single group of epoxyisoindole type, derived from the Diets-Alder addition, or else several of these groups of epoxyisoindole type.

The invention also relates to a process for synthesizing a crosslinking compound according to the invention, characterized in that it comprises a step of Diels-Alder addition reaction between a maleimide of formula (II)

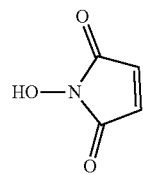

(II)

and a molecule of formula (III)

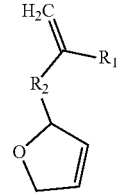

(III)

in which:
the group R$_1$ represents a hydrogen atom or an alkyl group bearing a linear or branched chain containing up to 6 carbon atoms;

the group $R_2$ represents a single bond or a group selected from: —$(C_1-C_6)$alkyl-, —$(C_2-C_6)$alkenyl-, —COO—, or —$(C_1-C_6)$alkyl-COO—, preferably —COO— or —$(C_1-C_6)$alkyl-COO—;

so as to form a Diels-Alder adduct;

and a step of reaction between said Diels Alder adduct with a molecule including at least one isocyanate function selected from the molecules of formula (IV) or of formula (V)

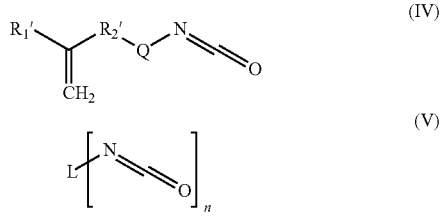
(IV)

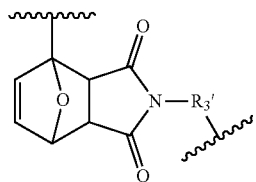
(V)

in which
the group $R_1'$ represents a hydrogen atom or an alkyl group bearing a linear or branched chain containing up to 6 carbon atoms;

the group $R_2'$ represents a single bond or a group selected from: —$(C_1-C_6)$alkyl-, —$(C_2-C_6)$alkenyl-, —COO—, or —$(C_1-C_6)$alkyl-COO—, preferably —COO— or —$(C_1-C_6)$alkyl-COO—;

the group Q represents -Z-L- in which
the group Z represents a single bond or the group L represents a single bond or a group selected from: —$(C_1-C_6)$alkyl-, —$(C_2-C_6)$alkenyl-, —$(C_2-C_6)$alkynyl-, —$(CONHR_4NHCOOR_5O)_m$—, —$(O-CO-NR_6)_m$—, —$(OR_4CHOHR_5)_m$—, —$(CH_2CHOHCH_2OR_4O)_m$—, —$(OR_4)_m$—, —$((CHOR_6)CH_2O-R4)_m$—, —$(R_4-COO-R_5)_m$—, —$NR_6$—, —$SO_2$—, —$SO_2NR_6$—, —O—, —S—, —$CONR_6$—, -aryl-, -(aryl-$R_4)_m$—, -(heteroaryl-$R_4)_m$—, —$((C_3-C_8)$heterocyclyl-$R_4)_m$—, —$((C_3-C_{14})$cycloalkyl-$R_4)_m$—, —$(C_1-C_6)$alkyl-$R_7$—$(C_1-C_6)$alkyl—, —$(C_2-C_6)$alkenyl-$R_7$—$(C_1-C_6)$alkyl-, —$(C_1-C_6)$alkyl-$R_7$—$(C_2-C_6)$alkenyl-, or —$(C_2-C_6)$alkenyl-$R_7$—$(C_2-C_6)$alkenyl-, in which the groups $R_4$ and $R_5$ represent a group selected from: single bond, —$(C_1-C_6)$alkyl-, —$(C_2-C_6)$alkenyl-, —$NR_6$—, —$SO_2$—, —$SO_2NR_6$—, —O—, —S—, —$CONR_4$—, -aryl-, -(aryl-$R_4)_m$—, -(heteroaryl-$R_4)_m$—, —$((C_3-C_8)$heterocyclyl)-$R_4)_m$—, —$((C_3-C_{14})$cycloalkyl-$R_4)_m$-aryl-, -heteroaryl-, —$(C_3-C_8)$heterocyclyl-, —$(C_3-C_{14})$cycloalkyl-, —$(C_1-C_6)$alkyl-OCO—, or —$CH_2$—$(CHOR_3)CH_2O$—$(C_1-C_6)$alkyl-;

in which $R_6$ represents a group selected from: hydrogen atom, —$(C_1-C_6)$alkyl, —$(C_2-C_6)$alkenyl, —$NH_2$, —COOH, —$SO_2H$, —OH, —SH, -aryl, -heteroaryl, —$(C_3-C_8)$heterocyclyl or —$(C_3-C_{14})$ cycloalkyl;

in which $R_7$ represents a group selected from: single bond, —$(CONHR_4NHCOOR_5O)_m$—, —$(O-CO-NR_4)_m$—, —$(COR_4)_m$—, —$(CH_2CHOHCH_2OR_4O)_m$—, —$(OR_4)_m$—, —$((CHOR_4)CH_2O-R_5)_m$—, —$(R_4-COO-R_5)_m$—, —$NR_6$—, —$SO_2$—, —$SO_2NR_4$—, —O—, —S—, —$CONR_4$—, -aryl-, -(aryl-$R_4)_m$—, -(heteroaryl-$R_4)_m$—, —$((C_3-C_8)$heterocyclyl)-$R_4)_m$—, —$((C_3-C_{14})$cycloalkyl-$R_4)_m$—, —$(C_1-C_6)$alkyl-OCO—, or —$CH_2$—$(CHOR_3)$ $CH_2O$—$(C_1-C_6)$alkyl-;

with n representing the number of repeating units, between 1 and 10, with m representing the number of repeating units, between 1 and 20, for example between 1 and 10.

This process for synthesizing a crosslinking compound according to the invention makes it possible to obtain a wide diversity of crosslinking compounds quickly and easily. In addition, when the synthetic process includes a purification step for removing the residues of compounds (II), (III), (IV) and (V), then it affords better performance, notably during use in compositions for thermoplastic polymer.

Furthermore, it has also been discovered that a composite part obtained via the manufacturing process has a significantly reduced content of residual monomer, due to better conversion of the monomer. The content of residual monomeric crosslinking compound is less than 5% relative to the amount of the monomer used.

Thus, the invention also relates to a composition comprising at least 80% of crosslinking compound of formula (I), preferably at least 90%, more preferably at least 95% and even more preferably at least 99%.

If the synthetic process is followed by a purification step and considering reagent ratios that are optimized to ensure a conversion of greater than 90%, as is presented in the present application, then this composition has the advantage of containing less than 5% of conjugated diene and dienophile functions (i.e. functions capable of undergoing a Diels-Alder addition reaction) that have not undergone a Diels-Alder addition reaction (i.e. free functions), This composition may, in a particularly advantageous manner, be used in a liquid composition intended for the formation of thermoplastic polymer. Thus, the crosslinking will be efficient and the polymer obtained will include little or no byproducts of free conjugated diene and dienophile type.

The invention also relates to a liquid composition comprising:
a. a (meth)acrylic polymer (P1),
b. a (meth)acrylic monomer (M1) or a blend of (meth)acrylic monomers, and
c. a crosslinking compound according to the invention.

This liquid composition, preferably of controlled viscosity, may be used in numerous industrial processes. It may undergo, after addition of at least one radical initiator, a rapid polymerization without the need to excessively increase the temperature.

By means of this crosslinking compound, the creation of a polymer network is not governed by the Diels-Alder addition kinetics, but only governed by the specific polymerization parameters of the two polymerizable vinyl functions present.

This composition also requires a low concentration of crosslinking compound and low concentrations are advantageous so as to have a thermoplastic polymer which can, at high temperature, be entirely de-crosslinked and fluidized. This allows accelerated and facilitated industrial manipulation.

In addition, the amount of free conjugated diene/dienophile compounds, which are capable of forming a Diels-Alder adduct, in the liquid composition according to the invention is less than 5 phr, preferably less than I phr, more preferably less than 0.1 phr relative to the sum of the (meth)acrylic monomer (M1) and of the (meth)acrylic polymer (P1). Thus, for a polymer formed from this liquid composition, this reduces the risks of subsequent reactivity or of leaching.

The invention also relates to a process for preparing a liquid composition according to the invention, said process including a first step of mixing a crosslinking compound according to the invention with a syrup comprising a (meth) acrylic monomer (M1) or a blend of (meth)acrylic monomers, and/or at least one (meth)acrylic polymer (P1). Advantageously, this first step corresponds to the dissolution of the crosslinking compound in a syrup comprising a (meth) acrylic monomer (M1) or a blend of (meth)acrylic monomers. Specifically, as shall be detailed hereinbelow, such mixing allows better dissolution of the crosslinking compound in the composition and better reversibility of the retro-Diels-Alder reaction. In this case, the process includes a second step of adding at least one (meth)acrylic polymer (P1) to the mixture prepared in the first step.

This preparation process may also include the addition of at least one radical initiator. This addition is preferably performed shortly before a polymerization step.

The invention also relates to the use of the liquid composition according to the invention for manufacturing formulations for the graphic arts such as inks or varnishes, for coatings, for adhesives such as structural adhesives, for paints such as road paints, for roof or floor sealings, for gelcoats or topcoats such as for artificial marbles, for chemical dowels or cement reinforcements.

The invention also relates to the use of the liquid composition according to the invention for manufacturing thermoplastic parts or manufacturing composite parts and also to the associated manufacturing processes.

These manufacturing processes are very rapid, in contrast with the current processes based. on crosslinking by conventional Diels-Alder addition reaction. In addition, they may be performed at moderate temperatures, i.e., for example, below 200° C.

The invention also relates to a polymeric composite material comprising a thermoplastic (meth)acrylic matrix and a fibrous substrate used as reinforcement, in which the fibrous substrate is constituted of long fibers, said composite material being characterized in that the thermoplastic (meth)acrylic matrix is obtained after polymerization of the liquid composition, said fibrous substrate being preimpregnated with the liquid composition according to the invention. The invention then also relates to a mechanical part or structural element constituted of the composite material according to the invention.

As has been mentioned, these polymeric composite materials may have the advantage of including little or no residues. Thus, this reduces the risks of subsequent reactivity or leaching.

Other advantages and features of the invention will become apparent on reading the following description given by way of illustrative and nonlimiting example, with reference to the appended figures, which depict:

FIG. 1, the kinetics of the Diels-Alder reaction at 60° C. monitored by $^1$H NMR between FMA and BMI, when the FMA:BMI ratio is 2:1 (triangles) or 4:1 (squares).

Figure 2:
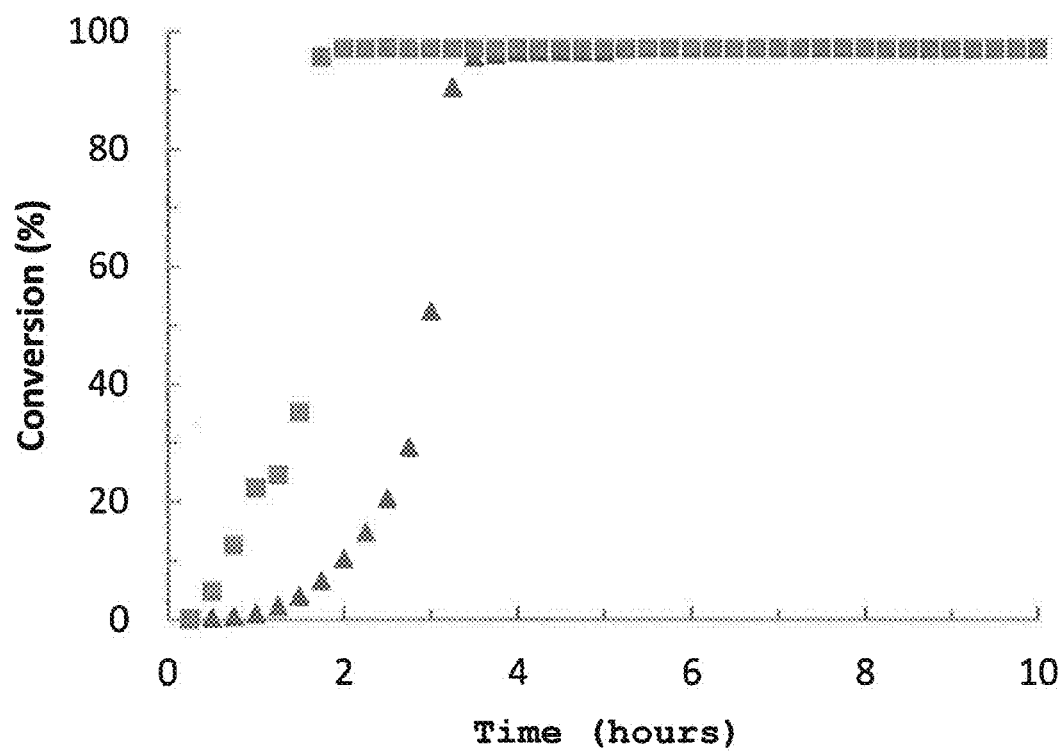

FIG. 2, the change in the degree of conversion as a function of time for the compositions containing 5 phr of crosslinking compound according to the invention with homogeneous suspension (square) or dissolution (triangle).

Figure 3:
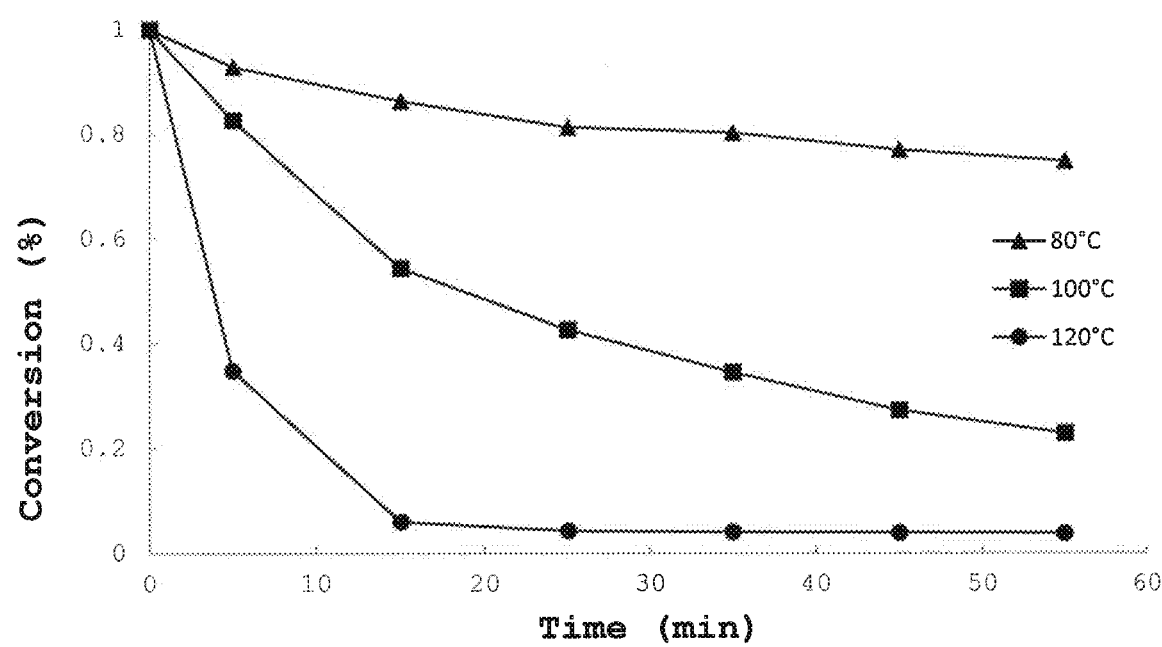

FIG. 3, the change in the degree of conversion as a function of time and at different temperatures during the retro-Diels-Alder reaction in deuterated DMF as monitored by $^1$H NMR.

DESCRIPTION OF THE INVENTION

The abbreviation "phr" denotes parts by weight per hundred parts of composition. For example, 1 phr of radical initiator in the composition means that 1 kg of radical initiator is added to 100 kg of composition.

The abbreviation "ppm" denotes parts by weight per million parts of composition. For example, 1000 ppm of a compound in the composition means that 0.1 kg of compound is present in 100 kg of composition.

For the purposes of the invention, the expression "polymer composite" denotes a multi-component material comprising at least two immiscible components, in which at least one 1.0 component is a polymer and the other component may be, for example, a fibrous reinforcement.

For the purposes of the invention, the term "fibrous reinforcement" or "fibrous substrate" means a plurality of fibers, unidirectional rovings or a continuous filament mat, fabrics, felts or nonwovens which may be in the form of strips, webs, braids, strands or parts.

The term "matrix" means a material serving as binder which is capable of transferring forces to the fibrous reinforcement. The "polymer matrix" includes polymers but may also include other compounds or materials. Thus, the "(meth)acrylic polymer matrix" relates to any type of compounds, polymers, oligomers, copolymers or block copolymers, both acrylic and methacrylic. However, it would not constitute a departure from the scope of the invention if the (meth)acrylic polymer matrix comprised up to 20% by weight, preferably less than 10% by weight, more preferably less than 5% by weight, of other nonacrylic monomers chosen, for example, from the group: butadiene, isoprene, styrene, substituted styrene, such as α-methylstyrene or tert-butylstyrene, cyclosiloxanes, vinylnaphthalenes and vinylpyridines.

The term "polymer" means either a copolymer or a homopolymer. The term "copolymer" means a polymer grouping together several different monomer units and the term "homopolymer" means a polymer grouping together identical monomer units. The term "block copolymer" means a polymer comprising one or more uninterrupted sequences of each of the separate polymer species, the polymer sequences being chemically different from each other and being bonded to each other via a covalent bond. These polymer sequences are also known as polymer blocks.

For the purposes of the invention, the term "radical initiator", denotes a compound that can start/initiate the polymerization of a monomer or monomers.

For the purposes of the invention, the term "polymerization" denotes the process of conversion of a monomer or of a blend of monomers into a polymer.

For the purposes of the invention, the term "monomer" denotes a molecule which can undergo a polymerization.

For the purposes of the invention, the term "thermoplastic polymer" means a polymer that is generally solid at room temperature, which may be crystalline, semicrystalline or amorphous, and which softens during an increase in temperature, in particular after passing its glass transition temperature (Tg) and flows at higher temperature and that may exhibit obvious melting on passing its "melting" point (Tm) (when it is semicrystalline) and which becomes solid again during a reduction in temperature below its melting point and below its glass transition temperature. This also applies to thermoplastic polymers slightly crosslinked by the presence of multifunctional monomers or oligomers in the formulation of the (meth)acrylate "syrup", in a mass percentage preferably of less than 10%, preferably less than 5%, and preferably less than 2%, which can be thermoformed when heated above the softening point.

For the purposes of the invention, the term "thermosetting polymer" means a plastic material which is irreversibly transformed by polymerization into an insoluble polymer network.

The term "(meth)acrylic monomer" means any type of acrylic and methacrylic monomer, The term "(meth)acrylic polymer" means a polymer essentially comprising (meth)acrylic monomers which represent at least 50% by weight or more of the (meth)acrylic polymer.

For the purposes of the invention, the term "PMMA" denotes homo- and copolymers of methyl methacrylate (MMA), the weight ratio of MMA in the PMMA preferably being at least 70% by weight for the MMA copolymer.

The term "linear or branched alkyl group, containing up to 6 carbon atoms" as used in the present invention (also referred to as $C_1$-$C_6$ alkyl) corresponds to a linear or branched saturated hydrocarbon-based chain, containing from 1 to 6 carbon atoms or to a linear or branched unsaturated hydrocarbon-based chain containing from 2 to 6 carbon atoms. A linear or branched saturated hydrocarbon-based chain containing from 1 to 6 carbon atoms comprises, without being limited thereto, methyl, ethyl, n-propyl, isopropyl, n-butyl, isobutyl, sec-butyl, t-butyl, n-pentyl groups, and the like. A linear or branched unsaturated hydrocarbon-based chain containing from 2 to 6 carbon atoms comprises at least one double bond or one triple bond, and includes, without being limited thereto, ethene, propene, butene, pentene, ethenyl, propenyl, butenyl, pentenyl groups, and the like.

The term "aryl group" as used in the present invention denotes an aromatic hydrocarbon-based group preferably comprising 6 to 10 carbon atoms and comprising one or more, notably 1 or 2, fused rings, for instance a phenyl group or a naphthyl group. Advantageously, this denotes a phenyl group.

The term "—($C_1$-$C_6$ alkyl)aryl" as used in the present invention denotes an aryl group as defined above linked to the molecule via a $C_1$ to $C_6$ alkyl group as defined above. In particular, the —($C_1$-$C_6$ alkyl)aryl group according to the invention is a benzyl group. For the groups comprising two or more subgroups, the attachment is indicated by "—". For example, "—($C_1$-$C_5$ alkyl)aryl" denotes an alkyl radical linked to an aryl radical in which the alkyl is linked to the rest of the molecule. For the groups comprising an attachment at each end, for example "—($C_1$-$C_5$ alkyl)aryl-", this denotes an alkyl radical linked to an aryl radical in which the alkyl or the aryl are linked to the rest of the molecule and this also encompasses both a —($C_1$-$C_5$ alkyl)aryl- group and an -aryl($C_1$-$C_5$ alkyl)- group.

The groups according to the invention, for example the aryl group or the cycloalkyl group, may be optionally substituted according to the present invention with one or more groups chosen independently from the group consisting of alkyl, alkoxyl, hydroxyl, carboxyl and ester. Examples of optionally substituted phenyl groups are methoxyphenyl, dimethoxyphenyl and carboxyphenyl. Alternatively, they are substituted only if this is explicitly specified. The term "optionally substituted" as used herein means that any one of the hydrogen atoms may be replaced with a substituent, such as a carboxyl group.

The crosslinking compound according to the invention denotes a crosslinking compound of formula (I)

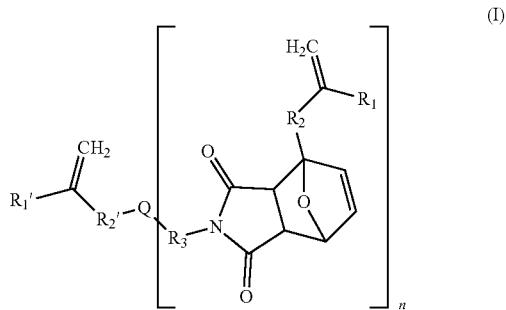

in which:
the group Q represents -Z-L- in which
the group Z represents a single bond or

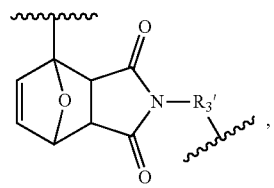

the group L represents a single bond or a group selected from: —($C_1$-$C_6$)alkyl-, —($C_2$-$C_6$)alkenyl-, —($C_2$-$C_6$)alkynyl-, —(CONHR$_4$NHCOOR$_5$O)$_m$—, —(O—CO—NR$_6$)$_m$—, —(OR$_4$CHOHR$_5$)$_m$—, —(CH$_2$CHOHCH$_2$OR$_4$O)$_m$—, —(OR$_4$)$_m$—, —((CHOR$_6$)CH$_2$O—R$_4$)$_m$—, —(R$_4$—COO—R$_5$)$_m$—, —NR$_6$—, —SO$_2$—, —SO$_2$NR$_6$—, —O—, —S—, —CONR$_6$—, -aryl-, -(aryl-R$_4$)$_m$—, -(heteroaryl-R$_4$)$_m$—, —(($C_3$-$C_8$)heterocyclyl-R$_4$)$_m$—, —(($C_3$-$C_{14}$)cycloalkyl—R$_4$)$_m$—, —($C_1$-$C_6$)alkyl-R$_7$—($C_1$-$C_6$)alkyl-, —($C_2$-$C_6$)alkenyl-R$_7$—($C_1$-$C_6$) alkyl-, —($C_1$-$C_6$)alkyl-R$_7$—($C_2$-$C_6$)alkenyl-, or —($C_2$-$C_6$)alkenyl-R$_7$—($C_2$-$C_6$)alkenyl-,
in which the groups R$_4$ and R$_5$ are identical or different and represent a group selected from: single bond, —($C_1$-$C_6$)alkyl-, —($C_2$-$C_6$)alkenyl-, —NR$_6$—, —SO$_2$—, —SO$_2$NR$_6$—, —O—, —S—, —CONR$_6$—, -aryl-, -(aryl-R$_6$)$_m$—, -(heteroaryl-R$_6$)$_m$—, —(($C_3$-$C_8$)heterocyclyl)-R$_6$)$_m$—, —(($C_3$-$C_{14}$)cycloalkyl-R$_6$)$_m$-aryl-, -heteroaryl-, —($C_3$-$C_8$)heterocyclyl-, —($C_3$-$C_{14}$)cycloalkyl-, —($C_1$-$C_6$)alkyl-OCO—, or —CH$_2$—(CHOR$_3$) CH$_2$O—($C_1$-$C_6$)alkyl-;
in which R$_6$ represent a group selected from: hydrogen atom, —($C_1$-$C_6$)alkyl, —($C_2$-$C_6$)alkenyl, —NH$_2$, —COOH, —SO$_2$H, —OH, —SH, -aryl, -heteroaryl, —($C_3$-$C_8$)heterocyclyl, or —($C_3$-$C_{14}$)cycloalkyl;

in which $R_7$ represents a group selected from: single bond, —(CONHR$_4$NHCOOR$_5$O)$_m$—, —(O—CO—NR$_4$)$_m$—, —(COR$_4$)$_m$—, —(OR$_4$)$_m$—, —(CH$_2$CHOHCH$_2$OR$_4$O)$_m$—, —((CHOR$_4$)CH$_2$O—R$_5$)$_m$—, —(R$_4$—COO—R$_5$)$_m$—, —NR$_6$—, —SO$_2$—, —SO$_2$NR$_6$—, —O—, —S—, —CONR$_6$—, -aryl-, -(aryl-R$_4$)$_m$—, -(heteroaryl-R$_4$)$_m$—, —((C$_3$-C$_8$)heterocyclyl)-R$_4$)$_m$—, —((C$_3$-C$_{14}$)cycloalkyl-R$_4$)$_m$—, —(C$_1$-C$_6$)alkyl-OCO—, or —CH$_2$—(CHOR$_3$)CH$_2$O—(C$_1$-C$_6$)alkyl-, the groups $R_1$ and $R_1'$ are identical or different and represent a hydrogen atom or an alkyl group bearing a linear or branched chain containing up to 6 carbon atoms;

the groups $R_2$ and $R_2'$ are identical or different and represent a single bond or a group selected from: —(C$_1$-C$_6$)alkyl-, —(C$_2$-C$_6$)alkenyl-, —COO—, or —(C$_1$-C$_6$)alkyl-COO—, preferably —COO— or —(C$_1$-C$_6$)alkyl-COO—;

the groups $R_3$ and $R_3'$ are identical or different and represent a single bond or a group selected from: —(C$_1$-C$_6$)alkyl-, —(C$_2$-C$_6$)alkenyl-, —NHCOO—, preferably —NHCOO—;

with n representing the number of repeating units, between 1 and 10, with m representing the number of repeating units, between 1 and 20, for example between 1 and 10.

Thus, the crosslinking compound according to the invention includes at least two polymerizable vinyl functions and at least one group of epoxyisoindole type, Diels-Alder adduct, which is capable of undergoing a retro-Diels-Alder reaction.

In particular, the crosslinking compound according to the invention may include only one group of epoxyisoindole type; the group Z then represents a single bond.

Alternatively, the crosslinking compound may include several groups of epoxyisoindole type. In this case, the group Z represents

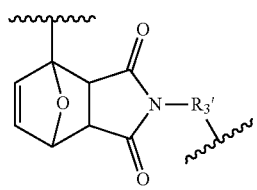

and n is between 1 and 10 and preferably between 1 and 5.

Preferably, the vinyl groups are (meth)acrylate groups, which are highly reactive in the context of polymerization reactions (the groups $R_3$ and $R_3'$ represent —COO— or —(C$_1$-C$_6$)alkyl-COO—).

Thus, the crosslinking compound is advantageously chosen from the group constituted of the compounds of formula (Ia)

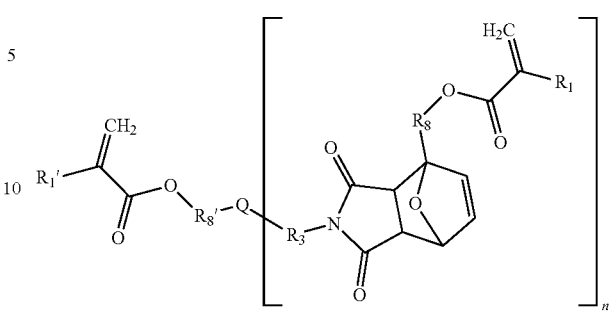

in which:

the groups $R_8$ and $R_8'$ are identical or different and represent a single bond or an alkyl group bearing a linear or branched chain containing up to 6 carbon atoms.

In particular, when the crosslinking compound includes only one group of epoxyisoindole type (Z is a single bond), the crosslinking compound is chosen from the group constituted of the compounds of formula (Ib)

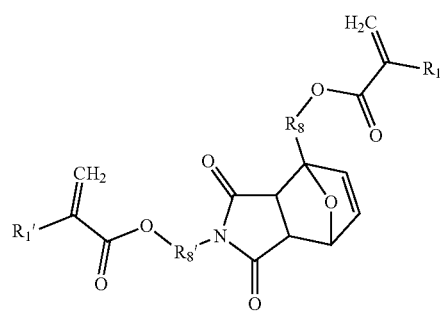

In particular, when the crosslinking compound includes at least two groups of epoxyisoindole type, the crosslinking compound is chosen from the group constituted of the compounds of formula (Ic)

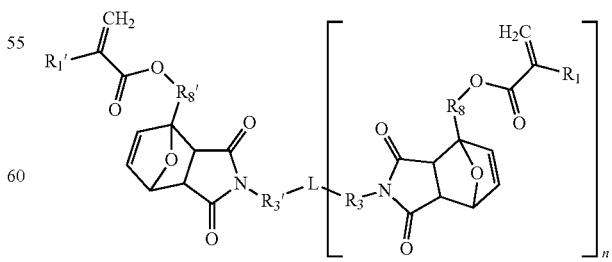

For example, the crosslinking compound may be chosen from the compound of formula (A) as represented below:

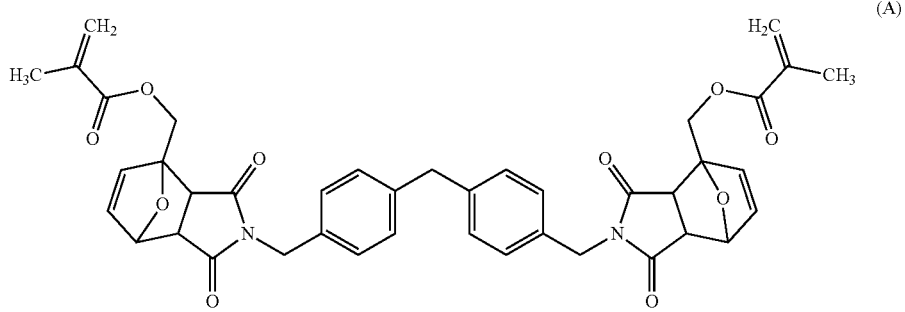 [SMILES: C=C(C)C(=O)OCC12C=CC(O1)C1C(=O)N(Cc3ccc(Cc4ccc(CN5C(=O)C6C7C=CC(COC(=O)C(=C)C)(O7)C6C5=O)cc4)cc3)C(=O)C12]

(A)

The groups of epoxyisoindole type, Diels-Alder adducts, are separated by a spacer "L". Advantageously, the Diels-Alder adducts are linked to this spacer via a urethane function generated during an isocyanate-hydroxyl reaction. Thus, preferably, the crosslinking compound is chosen from the group constituted of the compounds of formula (Id)

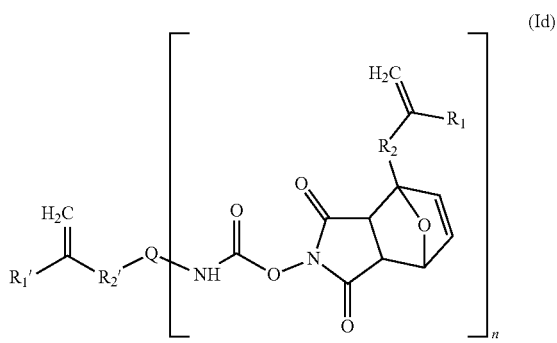

(Id)

In particular, the crosslinking compound includes only one group of epoxyisoindole type (Z is a single bond) and is chosen from the group constituted of the compounds of formula (Ie)

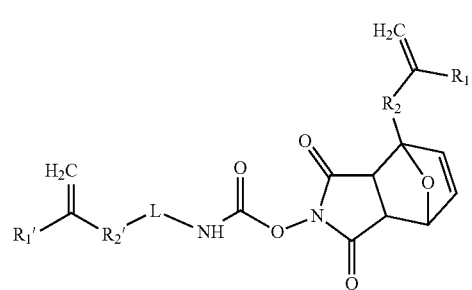

(Ie)

Alternatively, the crosslinking compound includes at least two epoxyisoindole functions and is chosen from the group constituted of the compounds of formula (If)

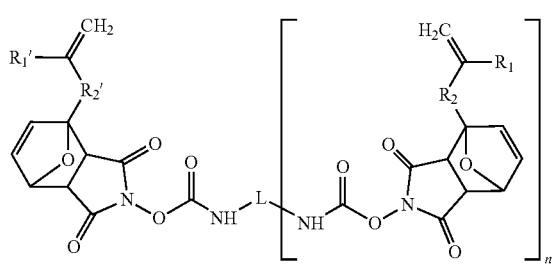

(If)

Even more preferably, the crosslinking compound according to the invention includes a urethane function generated, for example, during an isocyanate-hydroxyl reaction and (meth)acrylate functions. The crosslinking compound may then be chosen from the group constituted of the compounds of formula (Ig)

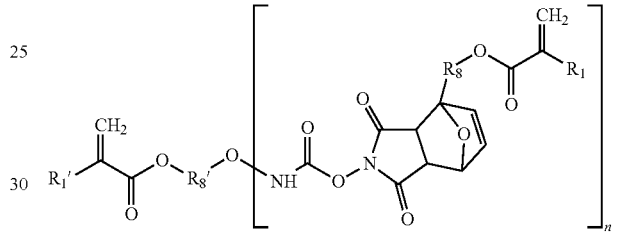

(Ig)

Even more preferably, the crosslinking compound according to the invention includes a urethane function generated, for example, during an isocyanate-hydroxyl reaction and (meth)acrylic functions. The crosslinking compound may then be chosen from the group constituted of the compounds of formula (Ig)

Alternatively, the crosslinking compound includes (meth)acrylic functions and only one epoxyisoindole function and is chosen from the group constituted of the compounds of formula (Ih)

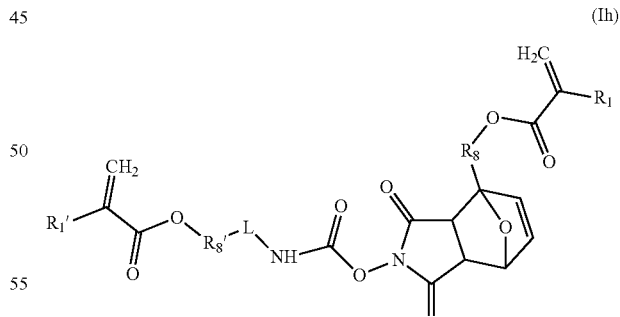

(Ih)

in which:
the groups $R_8$ and $R_8'$ are identical or different and represent a single bond or an alkyl group hearing a linear or branched chain containing up to 6 carbon atoms.

Alternatively, the crosslinking compound includes (meth)acrylic functions and at least two epoxyisoindole functions and is chosen from the group constituted of the compounds of formula (Ii)

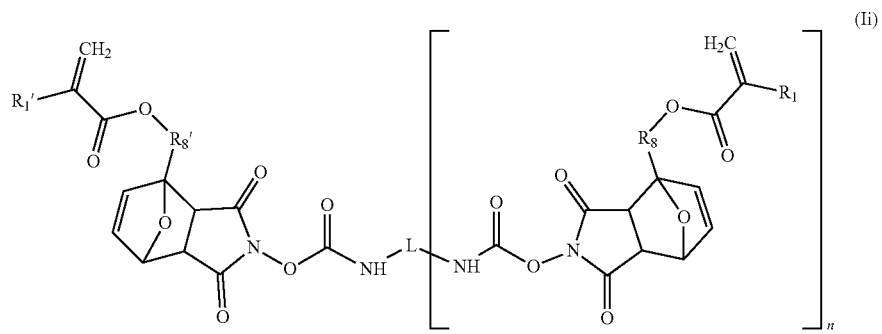
(Ii)
in which:
the groups $R_8$ and $R_8'$ are identical or different and represent a single bond or an alkyl group bearing a linear or branched chain containing up to 6 carbon atoms.
For example, the crosslinking compound may be chosen from the compound of formula (B) or of formula (C) as represented below:
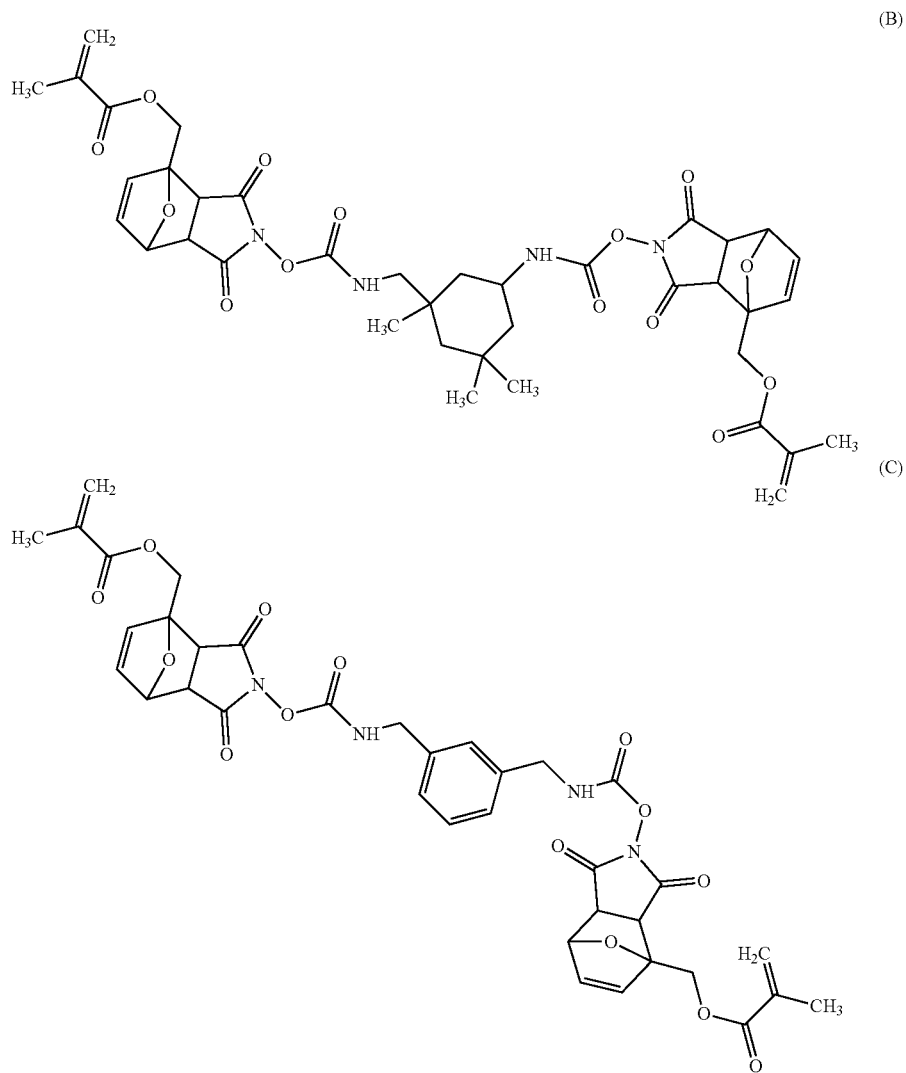

The crosslinking compound may be used as a homogeneous suspension or dissolved in a liquid composition and more particularly in a solution of (meth)acrylic monomer (M1) or a blend of (meth)acrylic monomers. Specifically, the inventors have shown that dissolution of the crosslinking compound makes it possible to obtain better reversibility of the crosslinking of a thermoplastic polymer including said crosslinking compound. Thus, advantageously, the crosslinking compound according to the invention has a solubility of greater than 20 g/L, preferably 40 g/L in a solution of (meth)acrylic monomer (M1) or a blend of (meth)acrylic monomers at 25° C. In the case of two liquids, the crosslinking compound according to the invention, when mixed with a solution of (meth)acrylic monomer (M1) or a blend of (meth)acrylic monomers at 25° C., forms only a single phase.

In particular, the crosslinking compound according to the invention has a retro-Diels-Alder temperature of greater than 150° C., preferably greater than 200° C.

In particular, the group L represents a group selected from: —$(C_1\text{-}C_6)$alkyl-, —$(C_2\text{-}C_6)$alkenyl-, —$(C_2\text{-}C_6)$alkynyl-, —$(CONHR_4NHCOOR_5O)_m$—, —$(O\text{—}CO\text{—}NR_6)_m$—, —$(OR_4CHOHR_5)_m$—, —$(CH_2CHOHCH_2OR_4O)_m$—, —$(OR_4)_m$—, —$((CHOR_6)CH_2O\text{—}R_4)_m$—, —$(R_4\text{—}COO\text{—}R_5)_m$—, —$NR_6$—, —$SO_2$—, —$SO_2NR_6$—, —O—, —S—, —$CONR_6$—, -aryl-, -(aryl-$R_4)_m$—, -(heteroaryl-$R_4)_m$—, —$((C_3\text{-}C_8)$heterocyclyl-$R_4)_m$—, —$((C_3\text{-}C_{14})$cycloalkyl-$R_4)_m$—, —$(C_1\text{-}C_6)$alkyl-$R_7$—$(C_1\text{-}C_6)$alkyl-, —$(C_2\text{-}C_6)$alkenyl-$R_7$—$(C_1\text{-}C_6)$alkyl-, —$(C_1\text{-}C_6)$alkyl-$R_7$—$(C_2\text{-}C_6)$alkenyl-, or —$(C_2\text{-}C_6)$alkenyl-$R_7$—$(C_2\text{-}C_6)$alkenyl-.

Preferably, the group L represents a group selected from: —$(C_1\text{-}C_6)$alkyl-, —$(C_2\text{-}C_6)$alkenyl-, —$(CONHR_4NHCOOR_5O)_m$—, —$(O\text{—}CO\text{—}NR_6)_m$—, —$(OR_4CHOHR_5)_m$—, —$(CH_2CHOHCH_2OR_4O)_m$—, —$(OR_4)_m$—, —$((CHOR_6)CH_2O\text{—}R_4)_m$—, —$(R_4\text{—}COO\text{—}R_5)_m$—, -aryl-, -(aryl-$R_4)_m$—, -(heteroaryl-$R_4)_m$—, —$((C_3\text{-}C_8)$heterocyclyl-$R_4)_m$—, —$((C_3\text{-}C_{14})$cycloalkyl-$R_4)_m$—, —$(C_1\text{-}C_6)$alkyl-$R_7$—$(C_1\text{-}C_6)$alkyl-, —$(C_2\text{-}C_6)$alkenyl-$R_7$—$(C_1\text{-}C_6)$alkyl-, —$(C_1\text{-}C_6)$alkyl-$R_7$—$(C_2\text{-}C_6)$alkenyl-, or —$(C_2\text{-}C_6)$alkenyl-$R_7$—$(C_2\text{-}C_6)$alkenyl-.

More preferably, the group L has a molar mass of at least 200 g/mol, preferably of at least 500 g/mol.

In particular, the groups $R_4$ and $R_5$ are identical or different and represent a group selected from: single bond, —$(C_1\text{-}C_6)$alkyl-, —$(C_2\text{-}C_6)$alkenyl-, —$NR_6$—, —$SO_2$—, —$SO_2NR_6$—, —O—, —S—, —$CONR_6$—, -aryl-, -(aryl-$R_6)_m$—, -(heteroaryl-$R_6)_m$—, —$((C_3\text{-}C_8)$heterocyclyl)-$R_6)_m$—, —$((C_3\text{-}C_{14})$cycloalkyl-$R_6)_m$-aryl-, -heteroaryl-, —$(C_3\text{-}C_8)$heterocyclyl-, —$(C_3\text{-}C_{14})$cycloalkyl-, —$(C_1\text{-}C_6)$alkyl-OCO—, or $CH_2$—$(CHOR_3)CH_2O$—$(C_1\text{-}C_6)$alkyl-.

In particular, the group $R_6$ may represent a group selected from: hydrogen atom, —$(C_1\text{-}C_6)$alkyl, —$(C_2\text{-}C_6)$alkenyl, —$NH_2$, —COOH, —$SO_2H$, —OH, —SH, -aryl, -heteroaryl, —$(C_3\text{-}C_8)$heterocyclyl, or —$(C_3\text{-}C_{14})$cycloalkyl, In particular, the group $R_7$ may represent a group selected from: single bond, —$(CONHR_4NHCOOR_5O)_m$—, —$(O\text{—}CO\text{—}NR_4)_m$—, —$(COR_4)_m$—, —$(OR_4)_m$—, —$(CH_2CHOHCH_2OR_4O)_m$—, —$((CHOR_4)CH_2O\text{—}R_5)_m$—, —$(R_4\text{—}COO\text{—}R_5)_m$—, —$NR_6$—, —$SO_2$—, —$SO_2NR_6$—, —O—, —S—, —$CONR_6$—, -aryl-, -(aryl-$R_4)_m$—, -(heteroaryl-$R_4)_m$—, —$((C_3\text{-}C_8)$heterocyclyl-$R_4)_m$—, —$((C_3\text{-}C_{14})$cycloalkyl-$R_4)_m$—, —$(C_1\text{-}C_6)$alkyl-OCO—, or —$CH_2$—$(CHOR_3)CH_2O$—$(C_1\text{-}C_6)$alkyl-.

The groups R1 and R1' are identical or different and represent a hydrogen atom or an alkyl group bearing a linear or branched chain containing up to 6 carbon atoms. Preferably, the groups R1 and R1' are identical or different and represent a hydrogen atom or an alkyl group bearing a linear chain containing up to 6 carbon atoms. More preferably, the groups R1 and R1' are identical or different and represent a hydrogen atom or a methyl.

The groups $R_2$ and $R_2'$ are identical or different and represent a single bond or a group selected from: —$(C_1\text{-}C_6)$alkyl-, —$(C_2\text{-}C_6)$alkenyl-, —COO—, —$(C_2\text{-}C_6)$alkyl-COO—. Preferably, the groups $R_2$ and $R_2'$ are identical or different and represent a —COO— or —$(C_1\text{-}C_6)$alkyl-COO— group. More preferably, the groups $R_2$ and $R_2'$ are identical or different and represent a —$(C_1\text{-}C_6)$alkyl-COO— group. Even more preferably, the groups $R_2$ and $R_2'$ represent a —$CH_2$—COO— group.

The groups $R_3$ and $R_3'$ are identical or different and represent a single bond or a group selected from: —$(C_1\text{-}C_6)$alkyl-, —$(C_2\text{-}C_6)$alkenyl-, —NHCOO—.

Preferably, the groups $R_3$ and $R_3'$ are identical or different and represent a single bond or an —NHCOO— group. Even more preferably, the groups $R_3$ and $R_3'$ represent an —NHCOO— group.

According to another aspect, the invention relates to a process for synthesizing the crosslinking compound according to the invention. The process comprises a step of Diels-Alder addition reaction between a maleimide of formula (II)

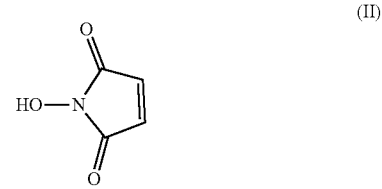

and a molecule of formula (III)

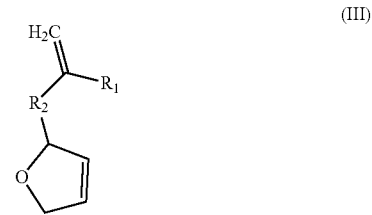

in which:
the group $R_1$ represents a hydrogen atom or an alkyl group bearing a linear or branched chain containing up to 6 carbon atoms;
the group $R_2$ represents a single bond or a group selected from: —$(C_1\text{-}C_6)$alkyl-, —$(C_1\text{-}C_6)$alkenyl-, —COO—, or —$(C_1\text{-}C_6)$alkyl-COO—, preferably —COO— or —$(C_1\text{-}C_6)$alkyl-COO—;
so as to form a Diels-Alder adduct;
and a step of reaction between said Diels-Alder adduct with a molecule including at least one isocyanate function selected from the molecules of formula (IV) or of formula (V)

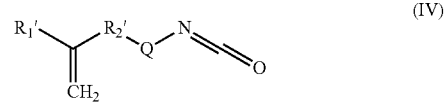

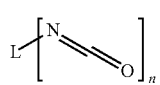
(V)

in which
the group Q represents -Z-L- in which
the group Z represents a single bond or

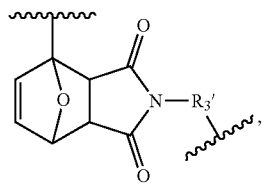

the group L represents a single bond or a group selected from: —($C_1$-$C_6$)alkyl-, —($C_2$-$C_6$)alkenyl-, —($C_2$-$C_6$)alkynyl-, —(CONHR4NHCOO$R_5$O)$_m$—, —(O—CO—N$R_6$)$_m$—, —(O$R_4$CHO$R_5$)$_m$—, —(C$H_2$CHOC$H_2$O$R_4$O)$_m$—, —(O$R_4$)$_m$—, —((CHO$R_6$)C$H_2$O—R4)$_m$—, —($R_4$—COO—$R_5$)$_m$—, —N$R_6$—, —S$O_2$—, —S$O_2$N$R_6$—, —O—, —S—, —CON$R_6$—, -aryl-, —(aryl-$R_4$)$_m$—, -(heteroaryl-$R_4$)$_m$—, —(($C_3$-$C_8$)heterocyclyl-$R_4$)$_m$—, —(($C_3$-$C_{14}$)cycloalkyl-$R_4$)$_m$—, —($C_1$-$C_6$)alkyl-$R_7$—($C_1$-$C_6$)alkyl-, —($C_2$-$C_6$)alkenyl-$R_7$—($C_1$-$C_6$)alkyl-, —($C_1$-$C_6$)alkyl-$R_7$—($C_2$-$C_6$)alkenyl-, —($C_2$-$C_6$)alkenyl-$R_7$—($C_2$-$C_6$)alkenyl-, in which the groups $R_4$ and $R_5$ represent a group selected from: single bond, —($C_1$-$C_6$)alkyl-, —($C_2$-$C_6$)alkenyl-, —N$R_6$—, —S$O_2$—, —S$O_2$N$R_6$—, —O—, —S—, —CON$R_4$—, -aryl-, —(aryl-$R_4$)$_m$—, -(heteroaryl-$R_4$)$_m$—, —(($C_3$-$C_8$)heterocyclyl)-$R_4$)$_m$, —(($C_3$-$C_{14}$)cycloalkyl-$R_4$)$_m$-aryl-, -heteroaryl-, —($C_3$-$C_8$)heterocyclyl-, —($C_3$-$C_{14}$)cycloalkyl-, —($C_1$-$C_6$)alkyl-OCO—, or —C$H_2$—(CHO$R_3$)C$H_2$O—($C_1$-$C_6$)alkyl-;

in which $R_6$ represents a group selected from: hydrogen atom, —($C_1$-$C_6$)alkyl-, —($C_2$-$C_6$)alkenyl-, —N$H_2$, —COOH, —S$O_2$H, —OH, —SH, -aryl, -heteroaryl, —($C_3$-$C_8$)heterocyclyl or —($C_3$-$C_{14}$)cycloalkyl;

in which $R_7$ represents a group selected from: single bond, —(CONHR4NHCOO$R_5$O)$_m$—, —(O—CO—N$R_4$)$_m$—, —(CO$R_4$)$_m$—, —(C$H_2$CHOC$H_2$O$R_4$O)$_m$—, —(O$R_4$)$_m$—, —((CHO$R_4$)C$H_2$O—$R_5$)$_m$—, —($R_4$—COO—$R_5$)$_m$—, —N$R_6$—, —S$O_2$—, —S$O_2$N$R_4$—, —O—, —S—, —CON$R_4$—, -aryl-, -(aryl-$R_4$)$_m$—, -(heteroaryl-$R_4$)$_m$—, —(($C_3$-$C_8$)heterocyclyl)-$R_4$)$_m$—, —(($C_3$-$C_{14}$)cycloalkyl-$R_4$)$_m$—, —($C_1$-$C_6$)alkyl-OCO—, or —C$H_2$—(CHO$R_3$)C$H_2$O—($C_1$-$C_6$)alkyl-.

This synthetic process advantageously makes it possible to obtain a crosslinking compound of formula (Ie) or of formula (Ii)

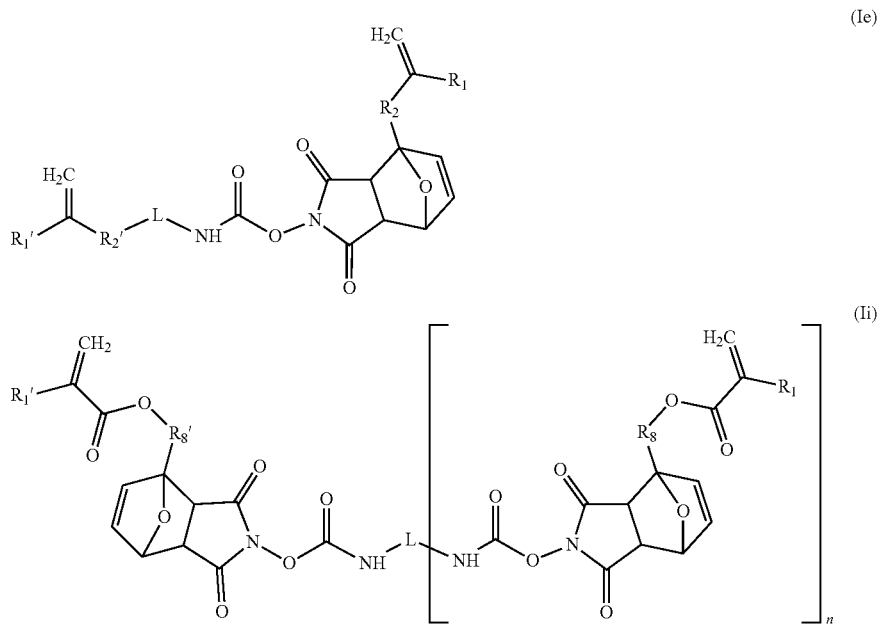

In a first stage, the reversible group is synthesized via a Diels-Alder addition reaction between a maleimide bearing a hydroxyl function (compound of formula (II)) and a furfuryl bearing a reactive function composed of formula (III). The Diels-Alder addition reaction between a maleimide of formula (II) and the furfuryl of formula (III) may be performed, for example, at 60° C. in the presence of tetrahydrofuran (THF).

Once the Diels-Alder product has been obtained, it becomes easy to react, in the presence of a catalyst, the hydroxyl functions on an isocyanate function of a molecule whose architecture, and notably the group L, will have been selected beforehand.

The use of a molecule comprising at least one isocyanate of formula (IV) or (V) makes it possible to achieve high yields based on urethane chemistry.

Advantageously, the mole ratio between the compounds of formula (III) and the compounds of formula (II) is greater than 2, preferably greater than or equal to 3 and even more preferably greater than or equal to 4. Specifically, it has been shown that an excess of furfuryl methacrylate leads to a higher reaction yield (≈98%).

In order to obtain a maximum degree of conversion, the reaction between the compounds of formula (III) and the compounds of formula (II) may have a duration of at least 5 hours, preferably of at least 10 hours, more preferably of at least 20 hours and even more preferably of at least 40 hours.

The synthetic process also includes a subsequent purification step directed toward removing the molecules of formula (II), (III) or (IV) which have not reacted to form the crosslinking compound. The purification processes may be selected, for example, from chromatography (e.g. adsorption) and precipitation.

The liquid composition or the (meth)acrylic syrup according to the invention comprises a (meth)acrylic polymer (P1), a (meth)acrylic monomer (M1) or a blend of (meth)acrylic monomers, and a crosslinking compound according to formula (I) according to the invention. The liquid composition according to the invention may also comprise at least one radical initiator.

The dynamic viscosity of the liquid composition or of the (meth)acrylic syrup is in a range from 10 mPa*s to 10 000 mPa*s, preferably from 20 mPa*s to 7000 mPa*s and advantageously from 20 mPa*s to 5000 mPa*s. The viscosity of the syrup may be readily measured with a rheometer or a viscometer. The dynamic viscosity is measured at 25° C. If the liquid (meth)acrylic syrup shows Newtonian behavior, i.e. without shear-thinning, the dynamic viscosity is independent of the shearing in a rheometer or the speed of the spindle in a viscometer. If the liquid composition shows non-Newtonian behavior, i.e. with shear-thinning, the dynamic viscosity is measured at a shear rate of 1 $s^{-1}$ at 25° C.

The liquid composition or the (meth)acrylic syrup according to the invention, for impregnating the fibrous substrate, in particular comprises a (meth)acrylic monomer or a blend of (meth)acrylic monomers, a (meth)acrylic polymer, crosslinking compound according to formula (I) according to the invention and at least one radical initiator.

Once polymerized, the (meth)acrylic monomer (M1) is converted into the (meth)acrylic polymer (P2) comprising the monomer units of (meth)acrylic monomer (M1).

The (meth)acrylic thermoplastic polymer has a glass transition temperature (Tg) of between 50° C. and 160° C., preferably between 70° C. and 140° C. and even more preferably between 90° C. and 120° C. Preferably, these temperatures are measured by differential scanning calorimetry according to the conditions specified in the standards ISO 11357-2/2013 for Tg and ISO 11357-3/2011 for Tm.

In addition, the (meth)acrylic thermoplastic polymer or a portion of the (meth)acrylic thermoplastic polymer has a melt flow index (MFI) according to ISO 1133 (230° C./3.8 kg) of less than 18 g/10 min. Preferably, the melt flow index is less than 18 g/10 min, more preferably less than 16 g/10 min, advantageously less than 13 g/10 min.

As regards the (meth)acrylic monomer (M1), the monomer is selected from acrylic acid, methacrylic acid, alkylacrylic monomers, alkylmethacrylic monomers, hydroxyalkylacrylic monomers and hydroxyalkylmethacrylic monomers, and mixtures thereof.

Preferably, the (meth)acrylic monomer (M1) is chosen from acrylic acid, methacrylic acid, hydroxyalkylacrylic monomers, hydroxyalkylmethacrylic monomers, alkylacrylic monomers, alkylmethacrylic monomers and mixtures thereof, the alkyl group containing 1 to 22 linear, branched or cyclic carbons; the alkyl group preferably containing from 1 to 12 linear, branched or cyclic carbons.

Advantageously, the (meth)acrylic monomer is chosen from methyl methacrylate, ethyl methacrylate, methyl acrylate, ethyl acrylate, methacrylic acid, acrylic acid, n-butyl acrylate, isobutyl acrylate, n-butyl methacrylate, isobutyl methacrylate, cyclohexyl acrylate, cyclohexyl methacrylate, isobornyl acrylate, isobornyl methacrylate, hydroxyethyl acrylate and hydroxyethyl methacrylate, and mixtures thereof.

According to a preferred embodiment, at least 50% by weight and preferably at least 60% by weight of the (meth) acrylic monomer is methyl methacrylate.

According to a first more preferred embodiment, at least 50% by weight, preferably at least 60% by weight, more preferably at least 70% by weight, advantageously at least 80% by weight and even more advantageously 90% by weight of the monomer is a mixture of methyl methacrylate with optionally at least one other monomer.

As regards the (meth)acrylic polymer (P1), mention may be made of polyalkyl methacrylates or polyalkyl acrylates. According to a preferred embodiment, the (meth)acrylic polymer is poly(methyl methacrylate) (PMMA).

The term "PMMA" denotes a methyl methacrylate (MMA) homopolymer or copolymer or mixtures thereof.

According to one embodiment, the methyl methacrylate (MMA) homo- or copolymer comprises at least 70%, preferably at least 80%, advantageously at least 90% and more advantageously at least 95% by weight of methyl methacrylate.

According to another embodiment, the PMMA is a mixture of at least one homopolymer and at least one copolymer of MMA, or a mixture of at least two homopolymers or two copolymers of MMA with a different average molecular weight or a mixture of at least two copolymers of MMA having a different composition of monomers.

The copolymer of methyl methacrylate (MMA) comprises from 70% to 99.7% by weight of methyl methacrylate and from 0.3% to 30% by weight of at least one monomer containing at least one ethylenic unsaturation that can copolymerize with methyl methacrylate.

These monomers are well known and mention may particularly be made of acrylic and methacrylic acids and alkyl (meth)acrylates in which the alkyl group contains from 1 to 12 carbon atoms. By way of examples, mention may be made of methyl acrylate and ethyl, butyl or 2-ethylhexyl (meth)acrylate. Preferably, the comonomer is an alkyl acrylate in which the alkyl group contains from 1 to 4 carbon atoms.

According to a first preferred embodiment, the copolymer of methyl methacrylate (MMA) comprises from 80% to 99.7%, advantageously from 90% to 99.7% and more advantageously from 90% to 99.5% by weight of methyl methacrylate and from 0.3% to 20%, advantageously from 0.3% to 10% and more advantageously from 0.5% to 10% by weight of at least one monomer, containing at least one ethylenic unsaturation, that can copolymerize with the methyl methacrylate. Preferably, the comonomer is chosen from methyl acrylate and ethyl acrylate, and mixtures thereof.

The weight-average molecular weight of the (meth) acrylic polymer (P1) should be high, i.e. greater than 50 000 g/mol and preferably greater than 100 000 g/mol.

The weight-average molecular weight may be measured by size exclusion chromatography (SEC).

The (meth)acrylic polymer is fully soluble in the (meth) acrylic monomer or in the blend of (meth)acrylic monomers. It enables the viscosity of the (meth)acrylic monomer or of the blend of (meth)acrylic monomers to be increased. The solution obtained is generally called a "syrup" or a "prepolymer". The dynamic viscosity value of the liquid (meth) acrylic syrup is between 10 mPa·s and 10 000 mPa·s. The viscosity of the syrup may be readily measured with a rheometer or a viscometer. The dynamic viscosity is measured at 25° C.

Advantageously, the liquid (meth)acrylic syrup contains no additional deliberately added solvent.

As regards the radical initiator, mention may be made of preferably water-soluble radical polymerization initiators or liposoluble or partially liposoluble radical polymerization initiators.

The water-soluble radical polymerization initiators are notably sodium, potassium or ammonium persulfates, used alone or in the presence of reducing agents such as sodium metabisulfites or hydrosulfites, sodium thiosulfate, sodium formaldehyde-sulfoxylate, a mixture of disodium salt of 2-hydroxy-2-sulfinoacetic acid, sodium sulfite and disodium salt of 2-hydroxy-2-sulfoacetic acid, or else a mixture of disodium salt of hydroxysulfinoacetic acid and disodium salt of hydroxysulfoacetic acid.

The liposoluble or partially liposoluble radical polymerization initiators are notably peroxides or hydroperoxides and derivatives of 1'-azobisisobutyronitrile. The peroxides or hydroperoxides are used in combination with the reducing agents described previously so as to lower their activation temperature.

The mass percentage of initiator relative to the total weight of monomer mixture is preferably between 0.05% by weight and 3% by weight, preferably between 0.1% by weight and 2% by weight.

Preferably, the (meth)acrylic liquid composition includes at least two radical initiators, at least one of which is heat-activated.

The liquid composition according to the invention may also, optimally, comprise a polymerization activator.

The polymerization activator or accelerator is chosen from tertiary amines such as N,N-dimethyl-p-toluidine (DMPT), N,N-dihydroxyethyl-p-toluidine (DHEPT), organic-soluble transition metal catalysts or mixtures thereof.

The liquid composition may also comprise one or more additives and/or one or more fillers, such as carbon-based fillers, mineral fillers and organic additives. All the optional additives and fillers are added to the liquid (meth)acrylic syrup before the impregnation and/or the polymerization.

The carbon-based fillers may in particular be active charcoal, natural anthracite, synthetic anthracite, carbon black, natural graphite, synthetic graphite, carbon-based nanofillers or mixtures thereof. They are preferably chosen from carbon-based nanofillers, in particular graphenes and/ or carbon nanotubes and/or carbon nanofibrils or mixtures thereof These fillers make it possible to conduct electricity and heat, and consequently make it possible to improve the lubrication of the polymer matrix when it is heated. They may then enable an increased reduction in cycle times or facilitate assembly, adjustment or repair at the installation site.

The mineral fillers notably include metal hydroxides, which are more particularly in the form of alumina trihydrate ($Al(OH)_3$) or magnesium hydroxide ($Mg(OH)$) or magnesium oxide (MgO), calcium hydroxides and mineral fillers such as calcium carbonate, titanium dioxide or silica or mineral nanofillers such as nanotitanium dioxides or nanosilicas.

As additives, mention may be made of organic additives such as impact strength modifiers (impact modifiers) or block copolymers, heat stabilizers, UV stabilizers, lubricants, viscosity modifiers, pH modifiers (sodium hydroxide), particle size modifiers (sodium sulfate), biocides, and mixtures thereof. These additives make it possible notably to improve the rheological, chemical and adhesion properties of the (meth)acrylic thermoplastic polymer matrix. The impact modifier is in the form of fine particles having an elastomeric core and at least one thermoplastic shell, the size of the particles being in general less than 1 μm and advantageously from 50 to 300 nm. The impact strength modifier is prepared by emulsion polymerization. The proportion of impact modifiers in the thermoplastic polymer matrix is 0 to 50%, preferably 0 to 25%, and advantageously 0 to 20% by weight.

The mass percentage of all of the additives and fillers relative to the total weight of (meth)acrylic thermoplastic polymer matrix is preferably less than 30%, preferably less than 10%.

Advantageously, the liquid (meth)acrylic composition does not contain any metal-based catalysts. No additive comprising a metal as activator to catalytically accelerate the polymerization reaction is added to the liquid (meth)acrylic composition according to the invention. This in particular concerns tin-based compounds such as tin chloride.

The content of the activator relative to the (meth)acrylic monomer (M1) of the liquid (meth)acrylic composition is from 100 ppm to 10 000 ppm (by weight), preferably from 200 ppm to 7000 ppm by weight and advantageously from 300 ppm to 4000 ppm.

In order to conserve a dynamic viscosity of the liquid composition or of the (meth)acrylic syrup, besides the fact that it allows good impregnation of the fibrous substrate, if necessary, and to conserve the thermoplastic properties of the matrix obtained after polymerization of the fibrous substrate preimpregnated with the syrup, the compounds of the syrup are incorporated in the following mass percentages:

The (meth)acrylic monomer(s) (M1) in the liquid composition or the (meth)acrylic syrup are present in proportions of between 40% and 90% by weight and preferably between 45% and 85% by weight of the composition comprising the (meth)acrylic monomer(s) (M1) and the (meth)acrylic polymer (P1).

The (meth)acrylic polymer(s) (P1) in the liquid composition or the (meth)acrylic syrup are present in a proportion of at least 1% by weight, preferably at least 5% and advantageously at least 10% by weight of the composition comprising the (meth)acrylic monomer(s) (M1) and the (meth)acrylic polymer (P1).

The (meth)acrylic polymer(s) (P1) in the liquid (meth) acrylic syrup are present in a proportion of not more than 50% by weight, preferably not more than 40% and advantageously not more than 30% by weight of the composition comprising the (meth)acrylic monomer(s) (M1) and the (meth)acrylic polymer (P1).

All the optional additives and fillers are added to the liquid (meth)acrylic syrup before the impregnation and/or the polymerization.

Advantageously, the amount of crosslinking compound according to the invention in the liquid composition is less than 10 phr, preferably less than 5 phr, relative to the sum of the (meth)acrylic monomer (M1) and of the (meth)acrylic polymer (P1). Specifically, such a proportion makes it possible to improve the reversibility of the Diels-Alder reaction in the crosslinked thermoplastic polymer. Advantageously, the amount of crosslinking compound according to the invention in the liquid composition is greater than 0.5 phi, relative to the sum of the (meth)acrylic monomer (M1) and of the (meth)acrylic polymer (P1). These concentrations may be adjusted as a function of the number of epoxyisoindole functions borne by the crosslinking compound and also as a function of the selected group L.

Advantageously, the liquid composition also comprises hydroxyethyl methacrylate for improving the solubility of the crosslinking compound in the liquid composition.

As regards the process for manufacturing the liquid composition or the (meth)acrylic syrup, said process includes a first step of mixing a crosslinking compound according to the invention with a syrup comprising the (meth)acrylic monomer (M1) or a blend of (meth)acrylic monomers and/or at least one (meth)acrylic polymer (P1).

This first step makes it possible to improve the distribution of the crosslinking compound in the composition to be polymerized. In addition, preferably, this first step makes it possible to dissolve the crosslinking compound according to the invention.

Preferably, the first step consists in preparing a first syrup comprising the (meth)acrylic monomer (M1) or a blend of (meth)acrylic monomers and the crosslinking compound according to the invention.

Specifically, the crosslinking compound according to the invention may be found in the liquid composition in the form of a homogeneous suspension or in dissolved form. The dissolved form is preferred since it allows better reversibility of the Diels-Alder reaction and thus better de-crosslinking of the thermoplastic polymer formed from the liquid composition.

Preferably, the process for manufacturing the liquid composition according to the invention includes a second step which consists in adding at least one (meth)acrylic polymer (P1) to the mixture prepared in the preceding step.

In particular, the process for manufacturing the liquid composition according to the invention includes a third step corresponding to the addition of at least one radical initiator.

The invention also relates to the use of the liquid composition according to the invention for manufacturing formulations for the graphic arts (e.g. ink for inkjet printing, overprinting varnish, screen ink, lithographic ink, flexography ink), for coatings (e.g. coatings for optical fibers, wood, metal, plastic, in cosmetic products), for adhesives (such as structural adhesives), for paints (such as road paints), for roof or floor sealing, for gelcoats or topcoats (for use, for example, in the motor vehicle or marine sector, wind turbines or artificial marbles), for chemical dowels or cement reinforcements.

The invention also relates to the use of the liquid composition according to the invention for manufacturing thermoplastic parts or manufacturing composite parts and also to the associated manufacturing processes.

Thus, in particular, the invention relates to a process for manufacturing thermoplastic parts, comprising the steps of placing the liquid composition according to the invention or prepared according to the preparation process according to the invention in polymerization means, and of initiating the polymerization.

Alternatively, in particular, the invention relates to a process for manufacturing composite parts, comprising the steps of impregnating fibers or a fibrous substrate with the liquid composition according to the invention or prepared according to the preparation process according to the invention in polymerization means, and of initiating the polymerization.

Preferably, the polymerization step is performed at a temperature below 200° C., preferably below 150° C. This makes it possible to not initiate the retro-Diels-Alder reaction and thus makes it possible rapidly to obtain a crosslinked polymer.

As regards the process for impregnating the fibers or the fibrous substrate, it comprises a step of impregnating the fibrous substrate with the liquid composition or the (meth)acrylic syrup.

This impregnation step may be performed in a mold or a closed mold or a bath.

If the viscosity of the liquid (meth)acrylic syrup at a given temperature is slightly too high for the impregnation process, it is possible to heat the syrup so as to obtain a more liquid syrup for sufficient wetting and correct and complete impregnation of the fibrous substrate.

As regards the fibrous substrate, mention may be made of a plurality of fibers, unidirectional ravings or a continuous filament mat, fabrics, felts or nonwovens which may be in the form of strips, webs, braids, strands or parts. The fibrous material may have various forms and dimensions, either one-dimensional, two-dimensional or three-dimensional. A fibrous substrate comprises an assembly of one or more fibers. When the fibers are continuous, the assembly thereof forms fabrics.

The one-dimensional form corresponds to linear long fibers. The fibers may be discontinuous or continuous. The fibers may be arranged randomly or parallel to each other, in the form of a continuous filament. A fiber is defined by its aspect ratio, which is the ratio between the length and the diameter of the fiber. The fibers used in the present invention are long fibers or continuous fibers. The fibers have an aspect ratio of at least 1000, preferably at least 1500, more preferably at least 2000, advantageously at least 3000 and more advantageously at least 5000, even more advantageously at least 6000, even more advantageously at least 7500 and most advantageously at least 10 000.

The two-dimensional form corresponds to nonwoven or woven fibrous mats or reinforcements or bundles of fibers, which may also be braided. Even if the two-dimensional form has a certain thickness and consequently in principle a third dimension, it is considered to be two-dimensional according to the present invention.

The three-dimensional form corresponds, for example, to stacked or folded nonwoven fibrous reinforcements or fibrous mats or stacked or folded bundles of fibers or mixtures thereof; an assembly of the two-dimensional form in the third dimension.

The origins of the fibrous material may be natural or synthetic. Natural materials that may be mentioned include plant fibers, wood fibers, animal fibers or mineral fibers.

Natural fibers are, for example, sisal, jute, hemp, linen, cotton, coconut, and banana fibers. Animal fibers are for example wool or fur.

Synthetic materials that may be mentioned include polymeric fibers chosen from fibers of thermosetting polymers, of thermoplastic polymers or mixtures thereof.

The polymeric fibers may consist of polyamide (aliphatic or aromatic), polyester, polyvinyl alcohol, polyolefins, polyurethanes, polyvinyl chloride, polyethylene, unsaturated polyesters, epoxy resins and vinyl esters.

The mineral fibers may also be chosen from glass fibers, in particular of type E, R or S2, carbon fibers, boron fibers or silica fibers.

The fibrous substrate of the present invention is chosen from plant fibers, wood fibers, animal fibers, mineral fibers, synthetic polymer fibers, glass fibers and carbon fibers, and mixtures thereof.

Preferably, the fibrous substrate is chosen from mineral fibers.

The fibres of the fibrous substrate have a diameter between 0.005 μm and 100 μm, preferably between 1 μm and 50 μm, more preferably between 5 μm and 30 μm and advantageously between 10 μm and 25 μm.

Preferably, the fibers of the fibrous substrate of the present invention are chosen from continuous fibers (meaning that the aspect ratio does not necessarily apply as for long fibers) for the one--dimensional form, or for long or continuous fibers for the two-dimensional or three-dimensional form of the fibrous substrate.

According to another additional aspect, the invention relates to a polymeric composite material comprising a thermoplastic (meth)acrylic matrix and a fibrous substrate used as reinforcement, in which the fibrous substrate consists of long fibers, said composite material being characterized in that the thermoplastic (meth)acrylic matrix is obtained after polymerization of said fibrous substrate pre-impregnated with said liquid composition according to the invention or the (meth)acrylic syrup.

Another aspect of the present invention is a process for manufacturing thermoplastic parts, comprising the following steps:
  i) placing the liquid composition or the (meth)acrylic syrup in polymerization means, and
  ii) polymerizing the liquid composition or the (meth)acrylic syrup.

Another aspect of the present invention is a process for manufacturing mechanical or structured parts or products, comprising the following steps:
  i) impregnating a fibrous substrate with the liquid composition or (meth)acrylic syrup according to the invention,
  ii) polymerizing the liquid composition or the (meth)acrylic syrup impregnating said fibrous substrate.

As regards the process for manufacturing composite parts, but also mechanical or structured parts or products, various processes may be used for manufacturing these parts. Mention may be made of vacuum-assisted resin infusion (VARI), pultrusion, vacuum infusion molding, pressurized infusion molding, autoclave molding, resin transfer molding (RTM) and variants thereof such as (HP-RTM, C-RTM, I-RTM), reaction-injection molding (RIM), reinforced reaction-injection molding (R-RIM) and variants thereof, press molding, compression molding, liquid compression molding (LCM) or sheet molding (SMC) or bulk molding (BMC).

A first preferred manufacturing process for manufacturing composite parts is a process according to which the liquid composition is transferred onto the fibrous substrate by impregnation of the fibrous substrate in a mold. Processes requiring a mold are listed above and include the word molding.

A second preferred manufacturing process for manufacturing composite parts are processes according to which the liquid composition is used in the pultrusion process. The fibers are guided toward a hot die where a thermoplastic resin including the liquid composition according to the invention is injected. The fibers in the form of fibrous substrate are, for example, in the form of a unidirectional roving or a continuous filament mat. After impregnation in the resin batch, the wet fibers are pulled through a heated die, where the polymerization takes place.

A third preferred manufacturing process is vacuum-assisted resin infusion (VARI).

The process for manufacturing composite parts, but also mechanical or structured parts or products, may also comprise the step of post-forming. Post-forming comprises bending and also modifying the shape of the composite part.

The process for manufacturing composite parts, but also mechanical or structured parts or products, may also comprise the step of welding or adhesive bonding or rolling, The thermoplastic parts obtained via the processes according to the invention may be post-formed after polymerization of the liquid composition of the invention. Forming comprises bending and also modifying the shape of the composite part.

The manufactured thermoplastic parts or composite parts obtained after polymerization of the liquid composition of the invention and/or via the processes according to the invention may be welded, adhesively bonded or rolled.

As regards the use of the mechanical parts made of composite material thus manufactured, mention may be made of automotive applications, transport applications such as buses or lorries, nautical applications, railroad applications, sport, aeronautic and aerospace applications, photovoltaic applications, computer-related applications, construction and building applications, telecommunication applications and wind energy applications.

The mechanical part made of composite material is in particular a motor vehicle part, a boat part, a bus part, a train part, a sport article, a plane or helicopter part, a space ship or rocket part, a photovoltaic module part, a material for construction or building, for example composite armatures, dowels and callipers for civil engineering and high-rise construction, a wind turbine part, for example a girder spar cap of a wind turbine blade, a furniture part, a construction or building part, a telephone or cellphone part, a computer or television part, or a printer or photocopier part.

In a first preferred embodiment, the mechanical part made of composite material is, in particular, a construction or building material, for example composite armatures, dowels and callipers for civil engineering and high-rise construction.

In a second preferred embodiment, the mechanical part made of composite material is, in particular, a wind turbine part, for example a girder spar cap of a wind turbine blade.

In a third preferred embodiment, the mechanical part made of composite material is a motor vehicle structural part, such as a floor, a center pillar, a door rail, a side bracing, a seat rail or a forward shield.

EXAMPLES

First Step: Preparation of a Crosslinking Compound According to the Invention

The synthesis of the crosslinking compound according to the invention was performed with different ratios of conjugated diene compounds (e.g. furfuryl methacrylate—FMA) and dienophile bismaleimide). The reagents are introduced into a round-bottomed flask containing anhydrous tetrahydrofuran (THF). The reaction mixture is then placed under an inert atmosphere with stirring and the 1H NMR spectrum of the starting reaction mixture is monitored.

As presented in FIG. 1, the increase in the amount of FMA added to the reaction medium promotes the Diels-Alder addition reaction. Specifically, for a theoretical equimolar ratio, the reaction progresses very rapidly in the first hours, but tends to stagnate and to progress very slowly after 10 hours to reach a degree of conversion that is not greater than 75%. Nevertheless, it is particularly advantageous for all of the imide functions to be added so as to improve the subsequent crosslinking of the polymer of the thermoplastic polymer. Thus, it is particularly advantageous to use a large excess of FMA in order to further promote the reaction between the dienophile and the dienes borne by the FMA.

After having obtained a maximum degree of conversion after 48 hours, the reaction mixture is purified in order to remove the excess FMA present. The purification takes place by precipitation from ice-cold anhydrous methanol followed by filtration on a Büchner funnel. The product obtained is redissolved in a minimum amount of anhydrous THF solvent and then reprecipitated from methanol. The precipitate is stirred magnetically in the solvent for 30 minutes in order to extract the last traces of FMA. After filtration, the product is dried under vacuum at 25° C. overnight in order to extract the final traces of methanol.

Alternatively, the synthetic process includes a first synthetic step performed using FMA in the presence of hydroxymaleimide with a respective mole ratio of 4 to 1. Specifically, it has been shown that an excess of FMA led to a higher reaction yield (≈98%). The reaction takes place solvent-mediated in anhydrous THF, with stirring and under an inert atmosphere at 60° C. for 48 hours. The compound obtained is precipitated twice from cyclohexane and then, after filtration, it is dried for a few hours under vacuum at 50° C. A second synthetic step intended to form the crosslinking compound was performed by reaction between the Diels-Alder monoalcohol prepared previously and a compound including an isocyanate function. The two reagents are introduced stoichiometrically in the presence of THF to a proportion of 10% by mass of reagents. A catalyst, dibutyltin dilaurate—DBTDL, is incorporated in a proportion of 0.15% by mass. The solution is then stirred for 24 hours at 50° C. under an inert atmosphere. The reaction product obtained is then precipitated from cyclohexane. After filtration through a Büchner funnel, the product is dried for several hours under vacuum at 50° C.

Second Step: Preparation of a Liquid Composition or of the (Meth)Acrylic Syrup

A liquid composition is prepared by dissolving 25% by weight of PMMA (e.g. an MMA copolymer comprising ethyl acrylate as comonomer) as (P1) in 75% by weight of methyl methacrylate as (M1). To this liquid composition are added a crosslinking compound and a radical initiator.

As a function of the formulation of the liquid composition, the crosslinking compound may be soluble or may form a homogeneous suspension.

Third Step: Polymerization of a Liquid Composition or of the (Meth)Acrylic Syrup Various proportions of the crosslinking compound are added to the formulation P1 M1, respectively 0.5 phr, 2 phr, 5 phr and 10 phr relative to the amount of syrup used. The polymerization is then performed in a glass tube 5 mm in diameter temperature-regulated by means of a heating module. The respective compositions according to the invention are heated at a moderate temperature (60<T° C.<80) in a metal press under a pressure of 10 bar.

The synthesis of the copolymers is performed radical-mediated using low-viscosity syrups whose polymerization kinetics show rapid polymerization (<4 min) at moderate temperature (60<T° C.<80):

As is shown in FIG. 2, the addition of the crosslinking compound according to the invention has no influence on the polymerization of the various syrups. This thus makes it possible to conserve rapid kinetics with degrees of conversion, monitored by near-infrared spectrometry, of close to 100% achieved after polymerization times of less than 3-4 min.

Evaluation of the Performance

Evaluation of the Degree of Swelling

Evaluation of the degree of swelling provides additional information regarding the creation of a crosslinked network, but also an indication regarding the crosslinking density. Specifically, it may be assumed that a denser network will have a tendency to have a lower degree of swelling. For this, samples of mass ($m_{ini}$) are introduced into a few milliliters of THF for 72 hours.

After this period, the insoluble part is filtered off and then weighed, thus corresponding to the swollen network ($m_{sn}$). The THF containing the soluble fraction is placed in a rotary evaporator (rotavapor) so as to determine the mass of organic material dissolved ($m_{sol}$). The degree of swelling is then defined in the following manner:

$$\text{Degree of swelling } (\%) = \frac{m_{sn}}{m_{ini} - m_{sol}} \times 100$$

These analyses showed that the more the percentage of crosslinking compound increases, the smaller the degree of swelling of the polymer obtained. Thus, with an amount of compound of greater than 0.5 phr, a three-dimensional network is formed for which the crosslinking density can be varied by varying the concentration of crosslinking compound. For example, the degree of swelling obtained with 2 phr may be about 400% and about 320% with 5 phr of crosslinking compound. Similarly, it may be observed that, for an excessively small amount of the crosslinking compound (0.5 phr and less), the polymer obtained includes a crosslinked network, but said network is not a sufficiently dense network and ends up by disintegrating and being dissolved in the solvent.

Thermal Reversibility of the Diels-Alder Reaction

The crosslinking compound is dissolved in deuterated dimethylformamide and then introduced into a 5 mm NMR tube. The retro-DA reaction may then be monitored in situ by 1H NMR spectroscopy at various temperatures.

Thermoplastics have the property of having a flow threshold and also the capacity of being dissolved on contact with a suitable solvent. Thermosetting polymers, for their part, can neither flow nor be dissolved. As a result, knowing that the Diels-Alder reaction is particularly temperature-sensitive, it is impossible for us to use the flow properties as a determining factor. Consequently, it is by evaluating the solubility of the pseudo-thermoplastics in solvent medium that it is possible to determine the reversibility or otherwise of the copolymers obtained. For this, each copolymer synthesized is immersed in THF (solvent for the PMMA) so as to determine in a first stage the production or otherwise of a three-dimensional network (welling study). In a second stage, after having undergone the retro-Diels-Alder effect, the reversible or irreversible nature is determined by once again testing its solubility.

When a DA adduct is heated, it returns to its initial state to give BMI, on the one hand, and furfuryl methacrylate, on the other hand. This is confirmed in FIG. 3 showing the results of NMR monitoring at 100° C.

The kinetic monitoring of the retro-DA reaction makes it possible to confirm that the reversible aspect of the Diels-Alder addition depends greatly on the temperature. Specifically, as may be seen, the higher the temperature, the greater the retro-DA degree of conversion progresses strongly from the first moments. This is all the more true at and above 120° C., where, within the first minutes, virtually all of the crosslinking compounds have become dissociated in favor of the reformation of the initial BMI and FMA.

It may also be noted that at and above a certain amount of crosslinking compound, the various copolymers appear to have a reduced reversible nature. This is the case at and above an addition of 5 phr for a crosslinking compound that is soluble in the liquid syrup and for an addition of 10 phr of crosslinking compound in homogeneous suspension in the liquid syrup. Specifically, even after having reached the retro-Diels-Alder temperature, these formulations remain at least partially insoluble in THF and conserve a swollen polymer appearance. In the presence of a miscible initial mixture, it may be thought that the crosslinking points are homogeneously distributed within the polymer whereas they may be more centralized in the case of a heterogeneous mixture (suspension). When the crosslinking compound forms a homogeneous suspension, its solubility may be improved by adding hydroxyethyl methacrylate to the liquid composition.

Studies base their concepts of reversible polymers on the reaction of two compounds, one being constituted of furan side functions and the other being a bismaleimide. However, this study proposes the simple and efficient synthesis of a single compound. Specifically, during the use of multiple compounds, in addition to adding a constraint associated with the preparation of the conjugated diene+dienophile mixture, the result of the Diels-Alder addition cannot be correctly controlled notably with respect to its kinetics. As has been seen, these kinetics may be very long and furthermore greatly dependent on the temperature.

The advantage here of directly using a crosslinking compound lies in the fact that all the keys required for obtaining a reversible network are found in the form of a single, stable product which is easy to use. Furthermore, all of the molecules bear a reversible site ready for use, thus affording maximum efficacy. In addition, we have been able to see that this type of comonomer was entirely capable of being adapted to a rapid polymerization system, thus offering a wide range of applications. The polymerization of this type of compound is advantageously performed at a temperature below the retro-DA temperature. Producing a thermally reversible network also affords the polymer obtained improved resistance to chemical attack and notably to solvents, but also increases its heat resistance.

In addition, the use of a liquid composition according to the invention gives us a low-viscosity reaction mixture, which opens this system to numerous processes such as RTM or infusion, but also various applications, for instance adhesive formulations. Specifically, it would be possible in this way to assemble parts by adhesive bonding and then, on reaching the retro-DA temperature, they could be easily disassembled. Similarly, it is possible to use this reversible state in preimpregnated systems, SMC, etc. . . . in which the DA reaction could lead to a B-stage system and then, during molding, would allow flow by means of the retro effect and then the final polymerization by means of a high-temperature system.

The invention claimed is:
1. A liquid composition comprising:
a. a (meth)acrylic polymer (P1),
b. a (meth)acrylic monomer (M1) or a blend of (meth) acrylic monomers, and
c. a crosslinking compound of formula (I)

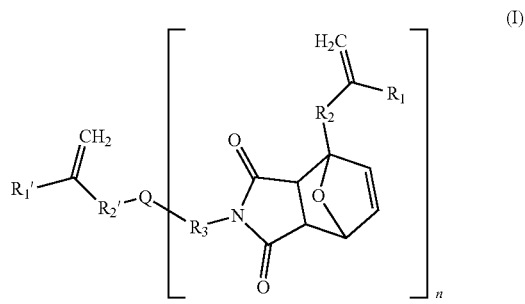

in which:
the group Q represents -Z-L- in which:
the group Z represents a single bond or

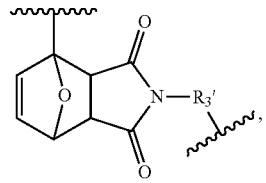

the group L represents a single bond or a group selected from: —($C_1$-$C_6$)alkyl-, —($C_2$-$C_6$)alkenyl-, —($C_2$-$C_6$)alkynyl-, —(CONHR$_4$NHCOOR$_5$O)$_m$—, —(O—CO—NR$_6$)$_m$—, —(OR$_4$CHOHR$_5$)$_m$—, —(CH$_2$CHOHCH$_2$OR$_4$O)$_m$—, —(OR$_4$)$_m$—, —((CHOR$_6$)CH$_2$O—R$_4$)$_m$—, —(R$_4$—COO—R$_5$)$_m$—, —NR$_6$—, —SO$_2$—, —SO$_2$NR$_6$—, —O—, —S—, —CONR$_6$—, -aryl-, -(aryl-R$_4$)$_m$-, -(heteroaryl-R$_4$)$_m$-, —((C$_3$-C$_8$)heterocyclyl-R$_4$)$_m$—, —((C$_3$-C$_{14}$)cycloalkyl-R$_4$)$_m$—, —(C$_1$-C$_6$)alkyl-R$_7$—(C$_1$-C$_6$)alkyl-, —(C$_2$-C$_6$)alkenyl-R$_7$—(C$_1$-C$_6$)alkyl-, —(C$_1$-C$_6$)alkyl-R$_7$—(C$_2$-C$_6$)alkenyl-, or —(C$_2$-C$_6$)alkenyl-R$_7$—(C$_2$-C$_6$)alkenyl-,
in which the groups R$_4$ and R$_5$ are identical or different and represent a group selected from: single bond, —(C$_1$-C$_6$)alkyl-, —(C$_2$-C$_6$)alkenyl-, —NR$_6$—, —SO$_2$—, —SO$_2$NR$_6$—, —O—, —S—, —CONR$_6$—, -aryl-, -(aryl-R$_6$)$_m$—, -(heteroaryl-R$_6$)$_m$—, —((C$_3$-C$_8$) heterocyclyl)-R$_6$)$_m$—, —((C$_3$-C$_{14}$)cycloalkyl-R$_6$)$_m$-aryl-, -heteroaryl-, —(C$_3$-C$_8$)heterocyclyl-, —(C$_3$-C$_{14}$) cycloalkyl-, —(C$_1$-C$_6$)alkyl-OCO—, or —CH$_2$—(CHOR$_3$)CH$_2$O—(C$_1$-C$_6$)alkyl-;
in which R$_6$ represents a group selected from: hydrogen atom, —(C$_1$-C$_6$)alkyl, —(C$_2$-C$_6$)alkenyl, —NH$_2$, —COOH, —SO$_2$H, —OH, —SH, -aryl, heteroaryl, —(C$_3$-C$_8$)heterocyclyl, or —(C$_3$-C$_{14}$)cycloalkyl;
in which R$_7$ represents a group selected from: single bond, —(CONHR$_4$NHCOOR$_5$O)$_m$—, —(O—CO—NR$_4$)$_m$—, —(COR$_4$)$_m$—, —(OR$_4$)$_m$—, —(CH$_2$CHOHCH$_2$OR$_4$O)$_m$—, —((CHOR$_4$)CH$_2$O—R$_5$)$_m$—, —(R$_4$—COO—R$_5$)$_m$—, —NR$_6$—, —SO$_2$—, —SO$_2$NR$_6$—, —O—, —S—, —CONR$_6$—, -aryl-, -(aryl-$R_4$)$_m$—, -(heteroaryl-$R_4$)$_m$—, —(($C_3$-$C_8$)heterocyclyl)-$R_4$)$_m$—, —(($C_3$-$C_{14}$)cycloalkyl-$R_4$)$_m$—, —($C_1$-$C_6$)alkyl-OCO—, or —$CH_2$—(CHOR$_3$)$CH_2$O—($C_1$-$C_6$)alkyl-;

the groups $R_1$ and $R_1'$ are identical or different and represent a hydrogen atom or an alkyl group bearing a linear or branched chain containing up to 6 carbon atoms;

the groups $R_2$ and $R_2'$ are identical or different and represent a single bond or a group selected from: —($C_1$-$C_6$)alkyl-, —($C_2$-$C_6$)alkenyl-, —COO—, or —($C_1$-$C_6$)alkyl-COO—;

the groups $R_3$ and $R_3'$ are identical or different and represent a single bond or a group selected from: —($C_1$-$C_6$)alkyl-, —($C_2$-$C_6$)alkenyl-, —NHCOO—;

with n representing the number of repeating units, between 1 and 10, with m representing the number of repeating units, between 1 and 20, and d. at least one radical initiator, wherein the at least one radical initiator comprises between 0.1% by weight and 2% by weight of the liquid composition, and wherein the amount of crosslinking compound in the composition is less than 10 phr, relative to the sum of the (meth)acrylic monomer (M1) and of the (meth)acrylic polymer (P1).

2. The liquid composition as claimed in claim 1, wherein said crosslinking compound is chosen from the group constituted of the compounds of formula (Ia)

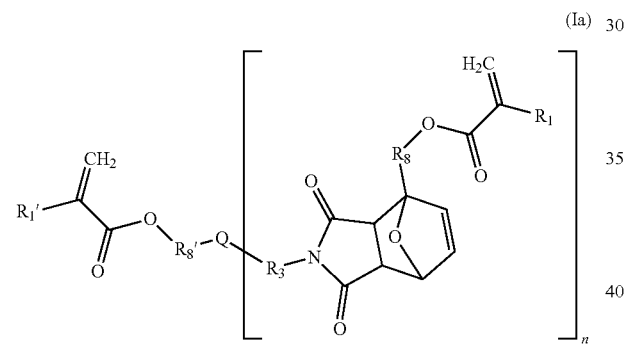

(Ia)

in which:
the groups $R_8$ and $R_8'$ are identical or different and represent a single bond or an alkyl group bearing a linear or branched chain containing up to 6 carbon atoms.

3. The liquid composition as claimed in claim 1, wherein said crosslinking compound is chosen from the group consisting of the compounds of formula (Ib)

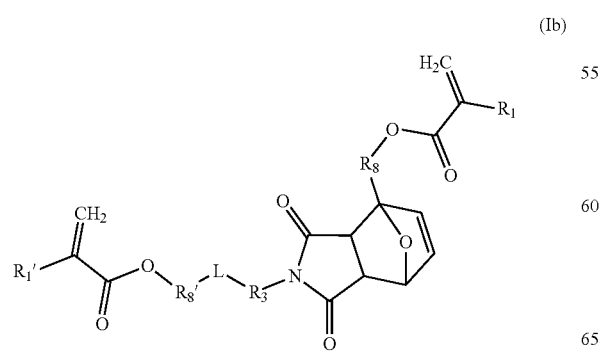

(Ib)

in which:
the groups $R_8$ and $R_8'$ are identical or different and represent a single bond or an alkyl group bearing a linear or branched chain containing up to 6 carbon atoms.

4. The liquid composition as claimed in claim 1, wherein said crosslinking compound is chosen from the group consisting of the compounds of formula (Ic)

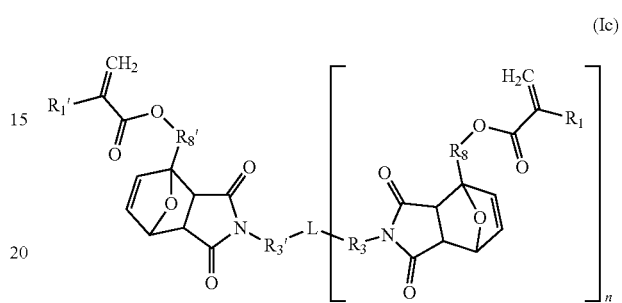

(Ic)

in which:
the groups $R_8$ and $R_8'$ are identical or different and represent a single bond or an alkyl group bearing a linear or branched chain containing up to 6 carbon atoms.

5. The liquid composition as claimed in claim 1, wherein said crosslinking compound is chosen from the group consisting of the compounds of formula (Id)

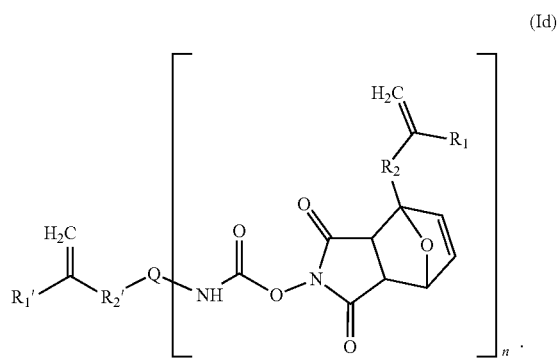

(Id)

6. The liquid composition as claimed in claim 1, wherein said crosslinking compound is chosen from the group consisting of the compounds of formula (Ie)

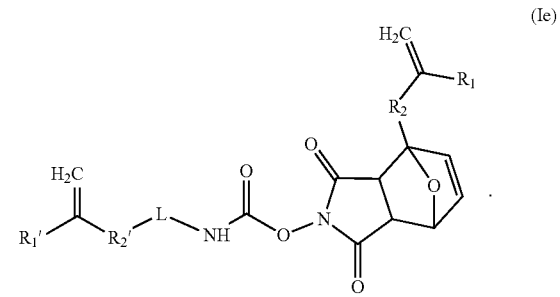

(Ie)

7. The liquid composition as claimed in claim 1, wherein said crosslinking compound is chosen from the group consisting of the compounds of formula (If)

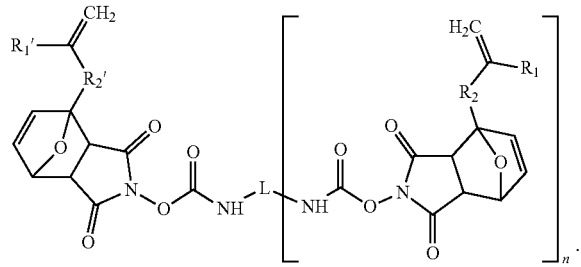

8. The liquid composition as claimed in claim 1, wherein said crosslinking compound is chosen from the group consisting of the compounds of formula (Ig)

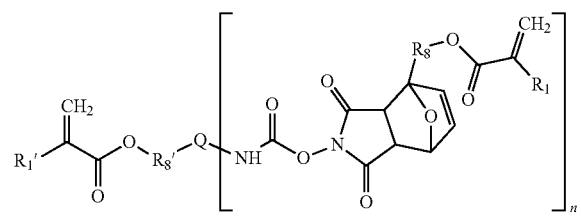

in which:
the groups $R_8$ and $R_8'$ are identical or different and represent a single bond or an alkyl group bearing a linear or branched chain containing up to 6 carbon atoms.

9. The liquid composition as claimed in claim 1, wherein said crosslinking compound is chosen from the group consisting of the compounds of formula (Ih)

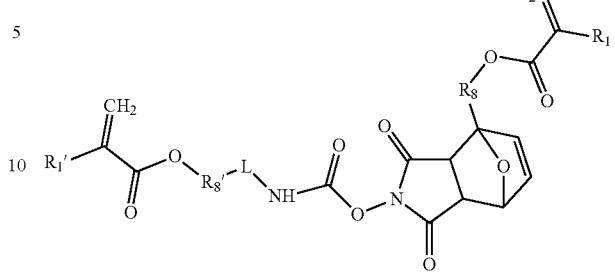

in which:
the groups $R_8$ and $R_8'$ are identical or different and represent a single bond or an alkyl group bearing a linear or branched chain containing up to 6 carbon atoms.

10. The liquid composition as claimed in claim 1, wherein said crosslinking compound is chosen from the group consisting of the compounds of formula (Ii)

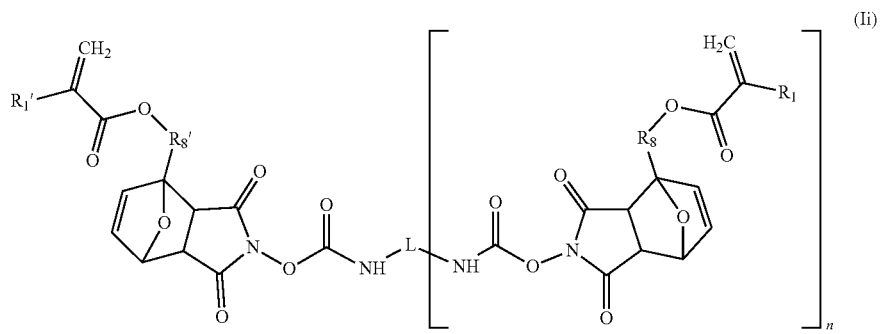

in which:
the groups $R_8$ and $R_8'$ are identical or different and represent a single bond or an alkyl group bearing a linear or branched chain containing up to 6 carbon atoms.

11. The liquid composition as claimed in claim 1, wherein said crosslinking compound has a solubility of greater than 20 g/L in a solution of (meth)acrylic monomer (M1).

12. The liquid composition as claimed in claim 1, wherein the group L has a molar mass of at least 200 g/mol.

13. The liquid composition as claimed in claim 1, wherein said crosslinking compound has a retro-Diels-Alder temperature of less than 150° C.

14. The liquid composition as claimed in claim 1, wherein said liquid composition has a dynamic viscosity of between 10 MPa*s and 10 000 mPa*s at 25° C.

15. The liquid composition as claimed in claim 1, wherein the (meth)acrylic polymer (P1) comprises at least 70% by weight of methyl methacrylate (MMA).

16. The liquid composition as claimed in claim 1, wherein the amount of free conjugated diene/dienophile compounds, capable of forming a Diels-Alder adduct, is less than 5 phr, relative to the sum of the (meth)acrylic monomer (M1) and of the (meth)acrylic polymer (P1).

17. The liquid composition as claimed in claim 1, wherein the groups R3 and R3' are different and represent a single bond or a group selected from: —(C1-C6)alkyl-, —(C2-C6)alkenyl-, —NHCOO— or the groups R3 and R3' are identical and represent a group selected from: —(C1-C6)alkyl-, —(C2-C6)alkenyl-, —NHCOO—.

18. A manufacturing formulation comprising the liquid composition of claim 1 wherein said formulation is selected from the group consisting of a graphic arts formulation, inks, varnishes, coatings, adhesives, structural adhesives, paints, road paints, roof or floor sealings, gelcoats, topcoats, artificial marbles, chemical dowels, cement reinforcements, a composition for the manufacture of thermoplastic parts and a composition for the manufacture of composite parts.

19. A process for manufacturing thermoplastic parts, comprising the following steps:
   i) placing the liquid composition as claimed in claim 1 in polymerization means, and
   ii) polymerizing.

20. The process for manufacturing thermoplastic parts of claim 19, wherein said thermoplastic parts are composite parts, further comprising the following steps:
   i) impregnating fibers or a fibrous substrate with the liquid composition as claimed in claim 1.

21. The manufacturing process as claimed in claim 19, wherein the polymerization step is performed at a temperature of less than 200° C.

22. The process as claimed in claim 21, wherein said process is selected from the group consisting of vacuum-assisted resin infusion (VARI), pultrusion, vacuum infusion molding, pressurized infusion molding, autoclave molding, resin transfer molding (RTM), HP-RTM molding, C-RTM molding, I-RTM molding, reaction-injection molding (RIM), reinforced reaction-injection molding (R-RIM) and variants thereof, press molding, compression molding, liquid compression molding (LCM), sheet molding (SMC), and bulk molding (BMC).

* * * * *